United States Patent
Eisen et al.

(10) Patent No.: US 11,241,177 B2
(45) Date of Patent: Feb. 8, 2022

(54) WRIST-SENSOR PULSE OXIMETRY DEVICE AND METHOD

(71) Applicant: Oxitone Medical Ltd., Kfar Saba (IL)

(72) Inventors: Leon Eisen, Kfar Saba (IL); Uzi Ben-Zion, Kfar Saba (IL); Koby Refael Gil, Kfar Saba (IL); Ofer Harpak, Kfar Saba (IL); Avi Shaham, Kfar Saba (IL)

(73) Assignee: Oxitone Medical Ltd., Kfar Saba (IL)

( * ) Notice: Subject to any disclaimer, the term of this patent is extended or adjusted under 35 U.S.C. 154(b) by 0 days.

(21) Appl. No.: 16/468,045

(22) PCT Filed: Dec. 15, 2017

(86) PCT No.: PCT/IB2017/058022
§ 371 (c)(1),
(2) Date: Jun. 10, 2019

(87) PCT Pub. No.: WO2018/116110
PCT Pub. Date: Jun. 28, 2018

(65) Prior Publication Data
US 2020/0015723 A1 Jan. 16, 2020

Related U.S. Application Data

(60) Provisional application No. 62/438,501, filed on Dec. 23, 2016.

(51) Int. Cl.
*A61B 5/1455* (2006.01)
*A61B 5/00* (2006.01)
*A61B 5/024* (2006.01)

(52) U.S. Cl.
CPC .......... *A61B 5/14552* (2013.01); *A61B 5/681* (2013.01); *A61B 5/6831* (2013.01);
(Continued)

(58) Field of Classification Search
CPC ......... A61B 5/145; A61B 5/68; A61B 5/6831; A61B 5/02427; A61B 5/6824; A61B 2562/185; A61B 5/6834
See application file for complete search history.

(56) References Cited

U.S. PATENT DOCUMENTS

| 6,443,906 | B1 | 9/2002 | Ting et al. | |
|---|---|---|---|---|
| 2010/0168531 | A1* | 7/2010 | Shaltis | A61B 5/02241 600/301 |

(Continued)

FOREIGN PATENT DOCUMENTS

CN 105919602 A 9/2016

OTHER PUBLICATIONS

International Search Report dated Nov. 5, 2018 for International Application No. PCT/IB2017/058022.
(Continued)

*Primary Examiner* — Allen Porter
*Assistant Examiner* — Abid A Mustansir
(74) *Attorney, Agent, or Firm* — Mintz Levin Cohn Ferris Glovsky and Popeo, P.C.

(57) ABSTRACT

A pulse oximetry device is provided that fixates generally around a user's wrist. The device may include one or more mechanical features that fix the device at, for example, a distal end of a wearer's ulna bone. The device may include one or more projections formed from a suitable material (e.g., elastomer such as silicon) that cause the device to fit snugly against the wearer's wrist and remain in place even when the wearer is moving, thus reducing motion artifacts in signals detected by the device. The device may include one or more mechanical features or fins that reduce ambient or stray light in the measurement area. The device may include one or more detectors, and one or more light sources, each having a different axis resulting from the manner in which
(Continued)

each is angled toward a virtual center point of the distal end of a wearer's ulna bone.

18 Claims, 28 Drawing Sheets

(52) U.S. Cl.
CPC ......... *A61B 5/02427* (2013.01); *A61B 5/6824* (2013.01); *A61B 2562/185* (2013.01)

(56) References Cited

U.S. PATENT DOCUMENTS

| | | | |
|---|---|---|---|
| 2010/0249554 A1 | 9/2010 | McKenna et al. | |
| 2014/0171766 A1 | 6/2014 | Ferris | |
| 2014/0200423 A1 | 7/2014 | Eisen et al. | |
| 2014/0228690 A1 | 8/2014 | Sato et al. | |
| 2014/0275852 A1* | 9/2014 | Hong | A61B 5/0205 600/301 |
| 2015/0073235 A1 | 3/2015 | Kateraas et al. | |
| 2016/0166153 A1* | 6/2016 | Woo | A61B 5/681 600/324 |
| 2016/0192744 A1* | 7/2016 | Partheban | G04G 17/00 224/164 |

OTHER PUBLICATIONS

Written Opinion of the International Searching Authority for International Application No. PCT/IB2017/058022.
National Intellectual Property Administration, P.R. China, Search Report, Appl. No. 201780087332.X, dated Sep. 22, 2021.

* cited by examiner

SECTION A-A
SCALE 1:1

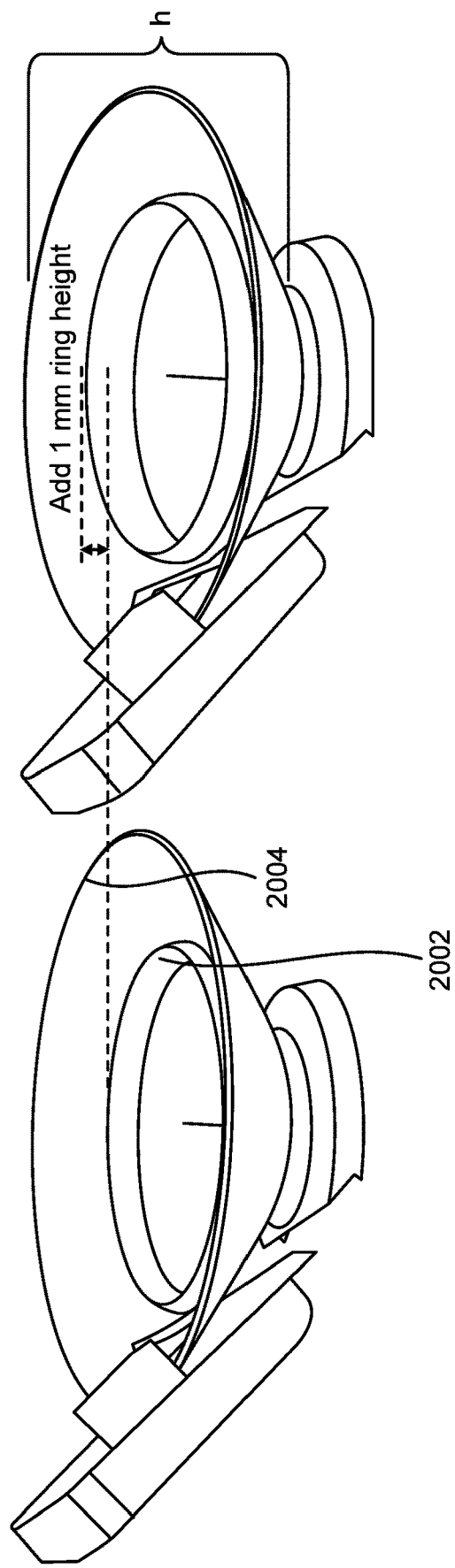

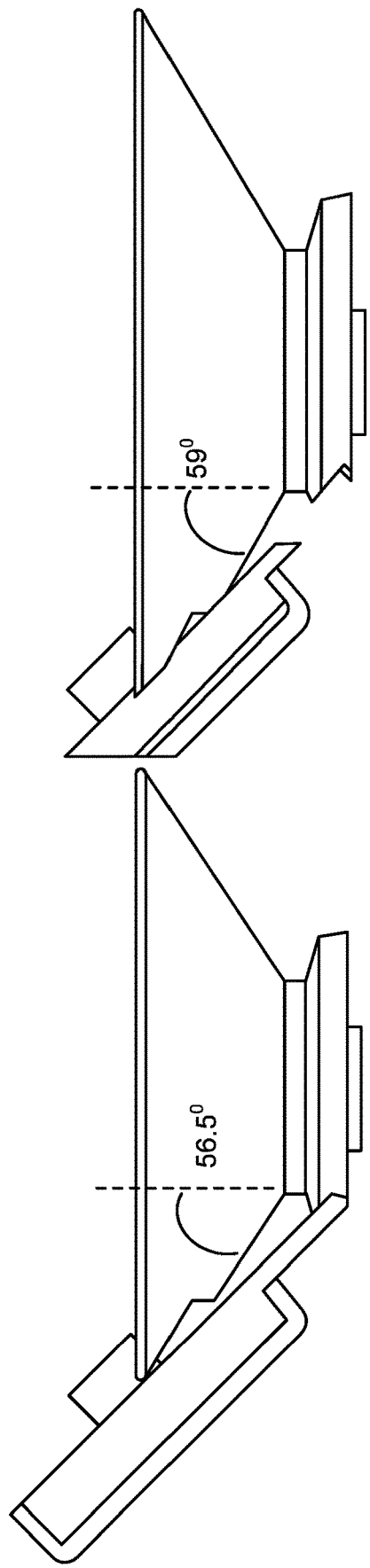

WRIST-SENSOR PULSE OXIMETRY DEVICE AND METHOD

CROSS-REFERENCE TO RELATED APPLICATION

This claims priority to U.S. Provisional Patent Application No. 62/438,501, filed Dec. 23, 2016, which is hereby incorporated by reference herein in its entirety.

TECHNICAL FIELD

Embodiments of the present invention relate to a device (e.g., pulse oximetry device) that can be worn on a wrist and associated methods.

BACKGROUND OF THE RELATED ART

This section is intended to introduce various aspects that may be related to embodiments of the present invention, which are described and/or claimed below. This discussion is believed to be helpful in providing background information to facilitate a better understanding of the various aspects of embodiments of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide patients, doctors, and other healthcare personnel with the information they need to secure the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood characteristics, such as the arterial blood oxygen saturation of hemoglobin (SPO2), and the rate of blood pulsations corresponding to each heartbeat of a patient. In fact, the "pulse" in pulse oximetry refers to the time varying amount of arterial blood at the measurement site during each cardiac cycle. Those skilled in the art will appreciate the pulse oximetry techniques used for obtaining the above physiological parameters which may also be termed photoplethysmography or, in short, PPG.

Pulse oximeters typically utilize a non-invasive optical sensor that detects the light response from within a patient's tissue indicative of the amount of light absorbed within the tissue at the illuminated site. One or more of the above physiological characteristics may then be calculated based upon the amount of the absorbed light. More specifically, the light passed through the tissue is typically selected to be of one or more light wavelengths that may be absorbed by the blood in an amount correlative to the amount of the hemoglobin constituent present in the blood. The amount of light absorbed at different light wavelengths may then be used to estimate the arterial blood hemoglobin related parameters using various algorithms. Pulsatile changes in the volume of the arterial blood at the illuminated site during blood pressure wave propagation alter the intensity of the light response detected by the sensor's photodetector.

The quality of the pulse oximetry measurement depends in part on the blood perfusion characteristics of the tissue illuminated by the light and in part on the magnitude of the pulsatile changes in the blood volume within the illuminated tissue. Pulse oximetry techniques typically utilize a tissue site that is well perfused with blood, such as a patient's finger, toe, or earlobe, on which to place the sensor.

For example, FIG. 1 illustrates a sensor 10 adapted to be placed on a finger 12 of a user, such as a patient, according to the prior art. The sensor 10 includes a clip formed of two portions 14 and 16 adapted to clip and constrain the sensor 10 to finger 12 while pulse oximetry measurements are taken. Sensors of a type similar to the sensor 10 are typically coupled to cables 18 that couple the sensor 10 to monitoring systems adapted to receive and process the signals from the sensor 10. Accordingly, such sensor using in continuous monitoring mode typically requires the patient (or user) to be confined to a certain area, in close vicinity of the monitoring system, thereby limiting patient mobility. In addition, pinch pressure applied by clip portions 14 and 16 on the finger 12 of the patient may overtime feel uncomfortable or become overbearing to the patient to the extent the patient may want to remove the sensor 10 and cease otherwise required monitoring. As a result, such sensors are not suitable for prolonged and continuous pulse oximetry measurements.

Further, as may occur with any physiological signals measuring device, the appearance of artifacts and other anomalies in the measured data can alter and/or degrade the quality of collected data to the extent that data may not be useful for providing reliable indication of occurring physiological processes. In that regard, pulse oximetry devices are no exception, as such devices may generally be prone to artifacts arising, for example, from patient motion, which may be random, voluntary or involuntary. Consequently, artifacts arising out of such circumstances can distort and skew obtained data, ultimately adversely affecting the quality of the pulse oximetry measurements. Although the accuracy and reliability of the physiological signals measurements is in large affected by the amount of blood perfusion, as well as by the distribution of the nonpulsatile blood within a tissue site, an increased or excessive amount of motion artifact can become a significant contributing factor to the overall pulse oximetry measurement. Due to the aforementioned facts, reflection geometry of the pulse oximetry measurements may not be applicable to various portions of user's body, such as those characterized as having weak blood perfusion, as well being prone to strong motion artifacts. In addition, such body portions may not be suitable for accommodating pulse oximetry devices employing forward transmission geometry in which light emitters and detector are disposed at opposite sides. In such a configuration, portions of the body from pulse oximetry measurements are desired may have tissue layers that are too thick for the light penetrate, thereby impeding the pulse oximetry measurements.

The following patent disclosures by the applicant are hereby incorporated by reference herein in their entireties: U.S. Pat. No. 9,314,197, titled "Wearable pulse oximetry device," and U.S. Pat. Nos. 8,868,149 and 9,149,216, each titled "Photoplethysmography device and method."

BRIEF SUMMARY OF EMBODIMENTS OF THE PRESENT INVENTION

In some embodiments of the present invention, a device (e.g., pulse oximetry device) and corresponding methods of use are provided.

For example, in some embodiments, a pulse oximetry device is provided that includes at least two light sources having different wavelengths, at least one detector responsive to said different wavelengths, a wrist strap, and a casing coupled to the wrist strap for housing the at least two light sources and the at least one detector. The wrist strap may include a projection (e.g., generally concave projection) adapted to fit snugly against a wearer's wrist and remain in place even when the wearer is moving. In some embodiments, the generally concave projection further comprises one or more ridges. In some embodiments, the generally concave projection includes an elastomer material (e.g., silicon) having a softness (durometer) of between 30 to 75 Shore A (e.g., approximately 50 Shore A). In some embodiments, the generally concave projection may include a hollow interior portion for receipt of medication.

In some embodiments, the wrist strap of a pulse oximetry device may include a first portion and a second portion adapted for attachment to the first portion (e.g., via a clasp) to fixate the wrist strap around a user's wrist. The first portion of the wrist strap may include the generally concave projection. The second portion of the wrist strap may include a second projection that assists to fixate the device at a fixated area corresponding to a distal end of the wearer's ulna bone. In some embodiments, the second projection is a curved projection that generally follows a contour of the wearer's ulna bone. In some embodiments, the second projection is formed generally in the shape of part of a dome or sphere.

In some embodiments, each of the at least two light sources and the at least one detector is positioned within the casing such that when the wrist strap is affixed around the wearer's wrist the least two light sources and the at least one detector are positioned adjacent to the distal end of the ulna and closer to the ulna than the radius, and the at least one detector is positioned to detect light emitted from the at least two light sources.

In some embodiments of the present invention, a pulse oximetry device is provided that includes at least two light sources having different wavelengths, at least one detector responsive to said different wavelengths, a wrist strap, and a casing coupled to the wrist strap for housing the at least two light sources and the at least one detector, wherein each of the at least two light sources and the at least one detector is angled generally toward a virtual center point of the distal end of a wearer's ulna bone and each of the at least two light sources and the at least one detector has a different axis.

In some embodiments, each of the at least two light sources and the at least one detector is positioned within the casing such that when the wrist strap is affixed around the wearer's wrist the least two light sources and the at least one detector are positioned adjacent to the distal end of the ulna and closer to the ulna than the radius, and the at least one detector is positioned to detect light emitted from the at least two light sources.

In some embodiments, at least one of the at least two light sources and the at least one detector of a pulse oximetry device includes a generally dome-shaped or conical-shaped structure that assists to fixate the pulse oximetry device, and its corresponding at least two light source(s) and at least one detector, at a fixated area at, adjacent to, or at a periphery of, a distal end of a wearer's ulna bone.

In some embodiments of the present invention, a pulse oximetry device is provided that includes at least two light sources having different wavelengths, at least one detector responsive to said different wavelengths, a wrist strap, and a casing coupled to the wrist strap for housing the at least two light sources and the at least one detector, wherein the casing comprises a first portion and a second portion that extend at an angle relative to each other. In some embodiments, a display may be fixed to the first portion of the casing, and the at least two light sources and the at least one detector may be fixed to the second portion of the casing. In some embodiments, the first portion of the casing and the second portion of the casing together generally resemble the shape of the letter "L." In some embodiments, the casing is strong enough to maintain the positioning of the at least two light sources and the at least one detector when the device is worn by a wearer, while simultaneously having slight pliability or elasticity to act as a movement dampening cushion that reduces measurement artifacts of the pulse oximetry device resulting from movement of the wearer.

In some embodiments, the casing includes a third portion that joins the first portion and the second portion of the casing, where the third portion allows for slight angular movement between the first portion and the second portion of the casing in response to normal forces while the pulse oximetry device is being worn by a user.

In some embodiments, the casing of the pulse oximetry device includes aluminum or thermoplastic urethane (TPU). In some embodiments, the casing has a durometer of between 25 Shore A and 35 Shore A.

In some embodiments, each of the at least two light sources and the at least one detector is positioned within the casing such that when the wrist strap is affixed around the wearer's wrist the least two light sources and the at least one detector are positioned adjacent to the distal end of the ulna and closer to the ulna than the radius, and the at least one detector is positioned to detect light emitted from the at least two light sources.

In some embodiments of the present invention, the pulse oximetry device may include a pad that is mounted or otherwise fixed generally to an inner side of the casing, wherein the pad includes one or more barriers that function to fit snugly against a wearer's wrist and prevent stray light from entering a measuring area of the at least two light sources and the at least one detector when the pulse oximetry device is worn by a wearer.

In various embodiments of the present invention, the at least two light sources and said at least one light detector of a pulse oximetry device may be disposed relative to one another such that emitted light is adapted to trans-illuminate via a wearer's ulna before reaching the at least one light detector. In other embodiments according to the present invention, the at least two light sources and the at least one light detector may be disposed relative to one another such that the emitted light is adapted to reach the at least one light detector in a reflective mode.

In various embodiments of the present invention, the at least two light sources of a pulse oximetry device may be selected from the group consisting of: LEDs having different wavelength ranges, laser diodes having different wavelengths, and a combination of LEDs and laser diodes having wavelengths outside the range of said LEDs.

In various embodiments of the present invention, the device may include a processor configured to calculate oximetry data and/or other data based at least in part on light detected by at least one detector.

Additional embodiments of the present invention are described below in connection with the Figures.

BRIEF DESCRIPTION OF THE DRAWINGS

For a better understanding of some embodiments of the present invention and to show how the same may be carried into effect, reference will now be made, by way of example, to the accompanying drawings in which like numerals designate corresponding elements or sections throughout. In the accompanying drawings:

FIGS. 19A, 19B, 20A, 20B, 21A, and 21B illustrate embodiments of light source configurations for a wrist-worn pulse oximeter according to some embodiments of the present invention;

DETAILED DESCRIPTION OF ILLUSTRATIVE EMBODIMENTS

Figure 1:
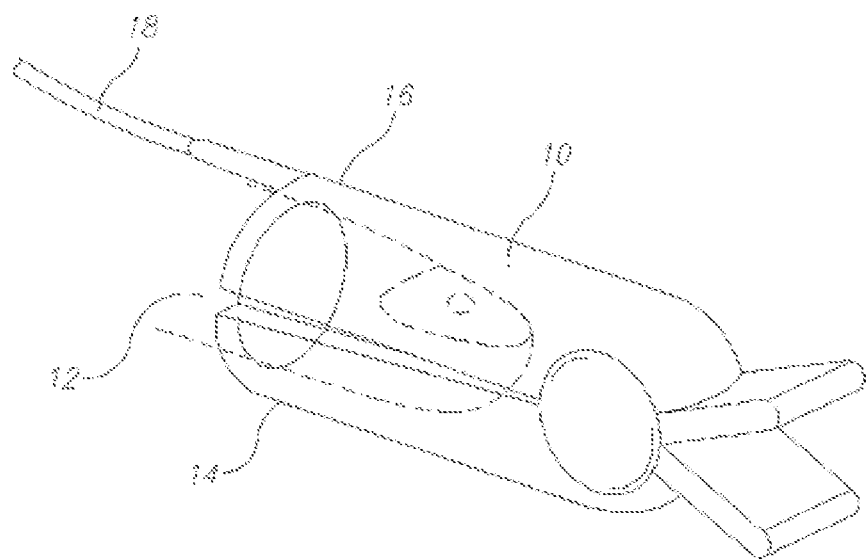
FIG. 1 is an illustration of a prior art pulse oximeter.

With specific reference now to the drawings in detail, it is to be understood that the particulars shown are by way of example and for purposes of illustrative discussion of preferred embodiments of the present invention only. The description taken in conjunction with the drawings will make apparent to those of ordinary skill in the art how the several forms and embodiments of the invention may be embodied in practice.

It is also to be understood that embodiments of the invention are not limited in their application to the details of construction and the arrangement of the components set forth in the following description or illustrated in the drawings. Embodiments of the invention may be practiced or carried out in various other ways. In addition, it is to be understood that the phraseology and terminology employed herein is for the purpose of description and should not be regarded as limiting.

Figure 2:
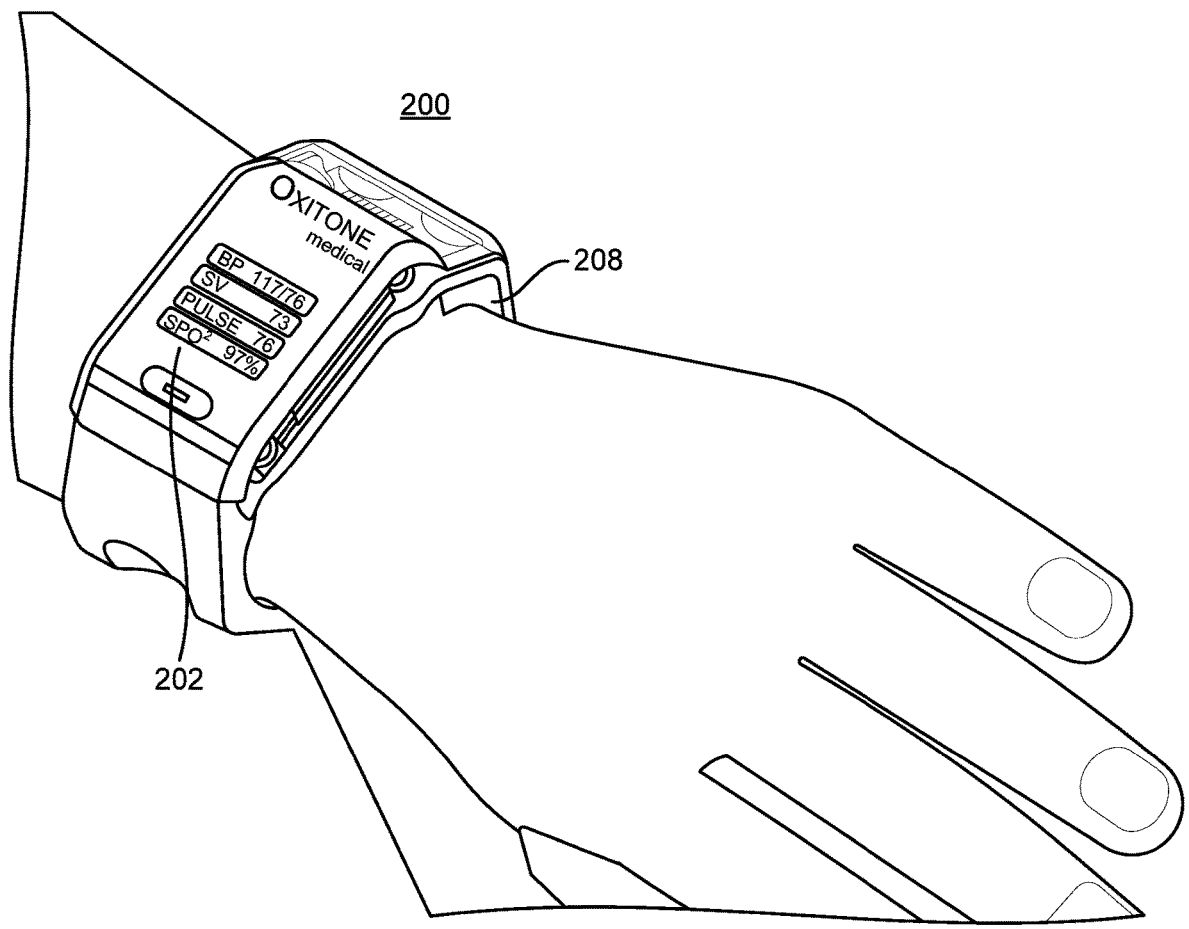
FIG. 2 is a perspective view of a device (e.g., wrist-type pulse oximeter) in accordance with an embodiment of the present invention.

Turning now to the figures, FIG. 2 is a perspective view of a device 200 in accordance with an exemplary embodiment of the present invention. Device 200 may be a wrist-type oximeter device adapted to be worn on a wrist of a user, as further shown in FIG. 2. In some embodiments, device 200 is adapted to obtain data including, for example, pulse data, oxygen saturation (SPO2) data, and/or other data from a user while the user wears device 200 on the wrist. Hence, a user can wear the device 200 in manner similar to that of wearing a watch, a wrist band or any article of clothing, ornament, or garment adapted to be worn on the wrist of the user. In this manner, a user can wear device 200 while performing any routine and ordinary operation the user would otherwise perform in everyday life, such as walking, running, cycling and so forth. In accordance with embodiments of the present technique, device 200 can be conveniently worn at any time or place by those users required to or wishing to obtain, for example, pulse oximetry and pulse rate data without being attached to elaborate monitoring device or being confined to certain monitoring areas. Thus, the device 200 is a self-contained, self-powered device adapted to obtain, analyze and process, for example, various light electromagnetic signals from which pulse oximetry data is ultimately obtained. Device 200 may further include wired or wireless interfaces whereby the device 200 can communicate and/or relay data signals to external and/or remote devices. Hence, in some embodiments, device 200 can collect and provide the oximetry data to any remote users, institutions such as hospitals or clinics, or anyone who requires or has interest in such pulse oximetry data of the user.

As illustrated in FIG. 2, device 200 may include a display 202 that displays, for example, data measured by device 200. Such data may include pulse rate data (e.g., "PULSE 76"), and data regarding the wearer's blood oxygen saturation of hemoglobin (e.g., "$SPO^2$ 97%"). In some embodiments, display 202 may be an LED display, such as, for example, an organic light-emitting diode ("OLED") display, liquid crystal display ("LCD"), or any other suitable display. In some embodiments, device 200 may include one or more physical buttons or user input interfaces (e.g., alphanumerical buttons or user interface where by the user can enter any combination of numbers and/or letters as desired or needed while the device is in use). Alternatively or additionally, in some embodiments, one or more buttons or user interface inputs may be placed at any side, or sides, of device 200 or any other area of device 200 that is accessible to the user. In some embodiments, device 200 may alternatively or additionally measure and/or display other data, including, for example, data regarding one or more vital signs, data regarding one or more blood analytes, blood pressure data (e.g., "BP 117/76"), and/or data regarding stroke volume (e.g., "SV 73").

Figure 3:
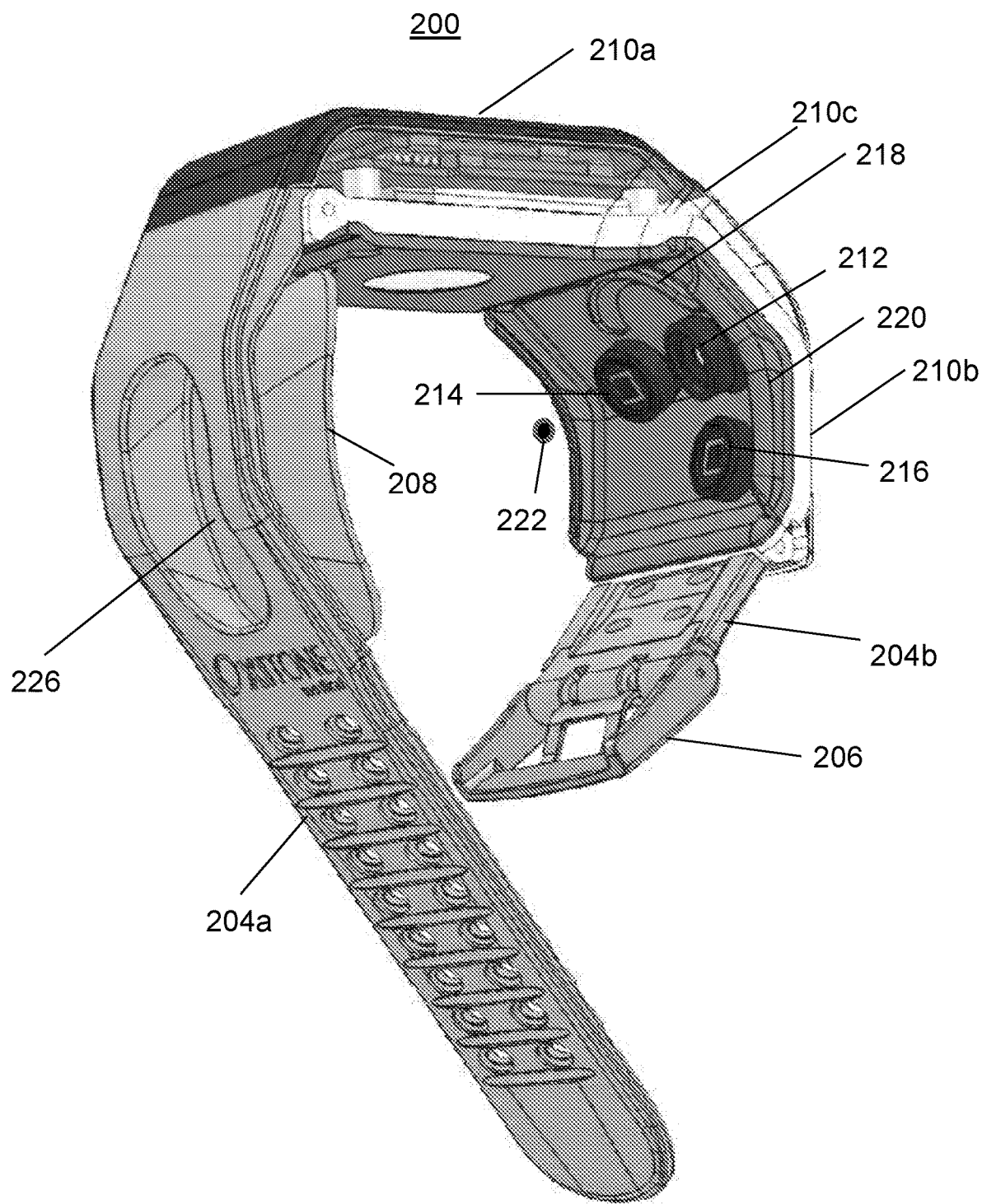
FIG. 3 is perspective view of the wrist-type pulse oximeter of FIG. 2, illustrating, for example, mechanical features for dampening the effects of a user's movement on sensor measurements and for fixating the device to a user's wrist, and showing a configuration of light source(s) and detector(s) according to some embodiments of the present invention.

As further illustrated by FIGS. 2 and 3, device 200 includes a wrist strap or band (204*a*, 204*b*) that is adapted to extend around a wearer's wrist. In some embodiments, the wrist band may be made up of any flexible and/or stretchable material, such as rubber, silicon, soft plastic, or cloth or any combination thereof for providing the user a comfortable fit and feeling while wearing the device 200. The wrist band may include first side 204*a* adapted to join with a second side 204*b* via a clasp 206, which may include, for example, a male attachment member for pairing with one or more suitable adjustment holes formed in wrist band 204*a* (as shown) based on the wearer's wrist size, a friction-fit clasp, or any other suitable attachment mechanism (e.g., hook and loop or velcro).

In some embodiments, wrist band 204*a* may include projection 208. Projection 208 may be adapted to dampen the effects of a wearer's movement on sensor measurements of device 200 and to fixate the device to a wearer's wrist when the two sides 204*a* and 204*b* of the wrist band are joined. In some embodiments, projection 208 may have an outer surface that is generally concave (see also e.g., FIGS. 4A, 12, and 14). Such a contour may enable projection 208, and thus device 200, to fit snugly against the wearer's wrist and remain in place even when the wearer is moving. In some embodiments, projection 208 may include, for example, one or more ridges 224 to further enable device 200 to fit snugly against the wearer's wrist and remain in place irrespective of whether the wearer is moving (see also e.g., FIGS. 4A, 12 and 14). Projection 208 may be made up of any flexible and/or stretchable material, such as rubber, silicon, soft plastic, or cloth or any combination thereof for providing the user a comfortable fit and feeling while wearing the device 200. For example, in some embodiments, projection 208 may be formed entirely from or otherwise include, at least in part (e.g., a coating), an elastomer material (e.g., silicon) having a softness (durometer) of between 30 to 75 Shore A (e.g., approximately 50 Shore A). In some embodiments, projection 208 may be at least partially hollow and may contain a space, for example, for storage of emergency medicine such as one or more pills for emergency intervention. In some embodiments, projection 208 may be integrally formed with or otherwise attached to wrist strap 204*a*. In some embodiments, wrist strap 204*a* may contain an opening or seal 226 through which the emergency medicine may be inserted and accessed (see also e.g., FIG. 5). The opening or seal 226 may open and close via any suitable mechanism, including, for example, a friction fit, a snap fit, a resealable membrane, or velcro.

In some embodiments, wrist straps 204*a* and 204*b* may couple to a casing (210*a*, 210*b*), which may house components including, for example, various electrical, mechanical, optical and other devices, such as batteries, processors, integrated circuit boards, one or more sensors, one or more light sources such as light emitting diodes, shunts, and/or other devices contributing to the functionality and integrity of the device 200. In some embodiments, display 202 (FIG. 2) may be mounted or otherwise fixed to a first, top portion 210*a* of the casing. In some embodiments, top portion 210*a* of the casing may house or otherwise include one or more (e.g., all) of the components in the block circuit diagram of FIG. 15, described below. In some embodiments, one or more light sources (e.g., 212), such as light emitting diodes (LEDs), and/or one or more sensors (e.g., 214 and/or 216), such as photo diodes, may be mounted to, fixed to, or otherwise housed by a second portion 210*b* of the casing. In some embodiments, the casing (e.g., rigid casing) when viewed from the side may be generally L-shaped in that second portion 210*b* may extend at an angle relative to first portion 210*a* of the casing generally around or at the side of a wearer's wrist (see also e.g., FIGS. 4*a* and 14). In some embodiments, the casing (210*a*, 210*b*) may be made up of any suitably strong and durable material, for example, metal or hard plastic, that is adapted for housing and protecting components of device 200 from external elements and forces. Casing (210*a*, 210*b*) may be suitably strong to maintain the positioning of light source(s) 212 and/or sensor(s) 214 and 216 of device 200. In some embodiments, the casing (210*a*, 210*b*) simultaneously may have slight pliability or elasticity to act as a movement dampening cushion that reduces measurement artifacts of device 200 resulting from movement of the wearer. For example, a joining interface (e.g., elbow) 210*c* between first portion 210*a* and second portion 210*b* of the casing may allow for slight angular movement between first portion 210*a* and second portion 210*b* in response to normal forces while device 200 is being worn by a user. For example, in some embodiments, casing (210*a*, 210*b*, 210*c*) may be formed entirely from or otherwise include aluminum and/or thermoplastic urethane (TPU) having a durometer of, for example, between 25 Shore A and 35 Shore A (e.g., approximately 30 Shore A). In some embodiments, all of portions 210*a*, 210*b*, and 210*c* may be integrally formed together, for example, as shown and described further below in connection with FIG. 14.

In some embodiments, device 200 may include structure 218 that assists to fixate device 200 at a fixated area corresponding to a distal end of the wearer's ulna bone, where the fixated area is used as a measuring area. Structure 218 may be a curved projection that is formed generally in the shape of part of a dome or sphere. In some embodiments, the measurement is carried out by a one or more sensors or detectors 214 and/or 216 positioned above or adjacent to the fixated area to detect light emitted by one or more light sources 212. For example, the light sources 212 may be two light sources having different wave lengths that are located at, above or adjacent to (e.g., at a periphery of) the fixated area. For example, light sources 212 may include a red light emitting diode (LED) for emitting light of wavelength 660 nm and an infrared LED for emitting light of wavelength 940 nm. In some embodiments, one or more of light source(s) 212, detector 214, and detector 216 may include a generally dome-shaped or conical-shaped structure that assists to fixate device 200, and its corresponding light source(s) and sensors, at a fixated area corresponding to a distal end of the wearer's ulna bone (see also e.g., FIGS. 4B and 20A, 20B, 21A, and 21B). In some embodiments, device 200 may include only one sensor (e.g., 214 or 216).

In some embodiments, structure 218 may be part of or integral to a pad that is mounted or otherwise fixed generally to an inner side of casing portion 210*b*. In some embodiments, some or all of the pad (e.g., including structure 218) may be formed entirely from or otherwise include a flexible and/or stretchable material, such as rubber, silicon, soft plastic, or cloth or any combination thereof for providing the user a comfortable fit and feeling while wearing the device 200. For example, in some embodiments, the pad (e.g., including structure 218) may be formed entirely from or otherwise include an elastomer material (e.g., silicon) having a softness (durometer) of between 30 to 75 Shore A (e.g., approximately 50 Shore A), which may be the same material that is used for projection 208. In some embodiments, the pad may include one or more barriers (e.g., fins) 220 that function to, for example, fit snugly against a wearer's wrist and/or to prevent ambient or stray light from entering the measuring area when device 200 is worn by a user. The pad may include, for example, a first barrier 220 on one side of the pad and a second barrier on a second, generally opposite side of the pad. For example, in some embodiments, each barrier 220 may be approximately 1 to 5 millimeters wide and extend approximately 1 to 5 millimeters mm outward from the user-facing surface of the pad. In some embodiments, the barriers 220 may extend along the entire, or any part(s) of, the sides of the pad.

In some embodiments, each of light source(s) 212 and sensor(s) 214 and/or 216 may generally face generally towards the distal end of the wearer's ulna bone when the device is worn by a user. In some embodiments, notwithstanding this general positioning, each of light source(s) 212 and sensor(s) 214 and/or 216 may have its own different and independent axis, for example, as reflected by unique x, unique y, and unique z coordinates and angular orientation relative to a virtual center point 222 of the distal end of a wearer's ulna bone (see also e.g., FIGS. 4A and 4B). In other words, in some embodiments, the line of sight or axis relative to the virtual center point 222 of the distal end of a wearer's ulna bone is asymmetrical for each of light source(s) 212 and sensor(s) 214 and/or 216. For example, in such embodiments, even though light source(s) 212 and sensor 214 are generally adjacent to one another, each has a different axis resulting from the manner in which each of 212 and 214 is angled generally toward the virtual center point 222 of the distal end of a wearer's ulna bone. As another example, even though light source(s) 212 and sensor 216 are generally adjacent to one another, each has a different axis resulting from the manner in which each of 212 and 214 is angled generally toward the virtual center point 222 of the distal end of a wearer's ulna bone.

In some embodiments, reflections of light from light source(s) 212 are measured by sensor(s) 214 and/or 216 at neither a reflection mode nor a transmission mode, but rather at an angle between, for example, 20° and 160° from the emitted light. This mode, termed trans-illumination, allows achieving an excellent signal to noise ratio that for the first time enables continuous and reliable measurement of oximetry data on the wrist. The term "trans-illumination" as used herein, is a mode of optical measurement, in which the measured light is reflected off a surface at an angle larger than 0° (which correspond to simple reflection) and smaller than 180° (which correspond to simple transmission). Commonly, but not exclusively, the reflection angles in trans-illumination mode are between approximately 20° and approximately 160°. In trans-illumination mode, the measured light is emitted from the light source, hits the reflective surface, which may be curved, at an angle, and is reflected at an angle to the detector. In practice, trans-illumination includes light going over various light paths, having in common an origin in the light source and a measurement in the detector. In other embodiments, reflections of light from light source(s) 212 are measured by sensor(s) 214 and/or 216 in a reflection mode. In some embodiments, reflections of light from light source(s) 212 are measured by one of sensor(s) 214 and/or 216 in a transillumination mode, and by the other of sensor(s) 214 and/or 216 in a reflection mode.

Figure 4A:
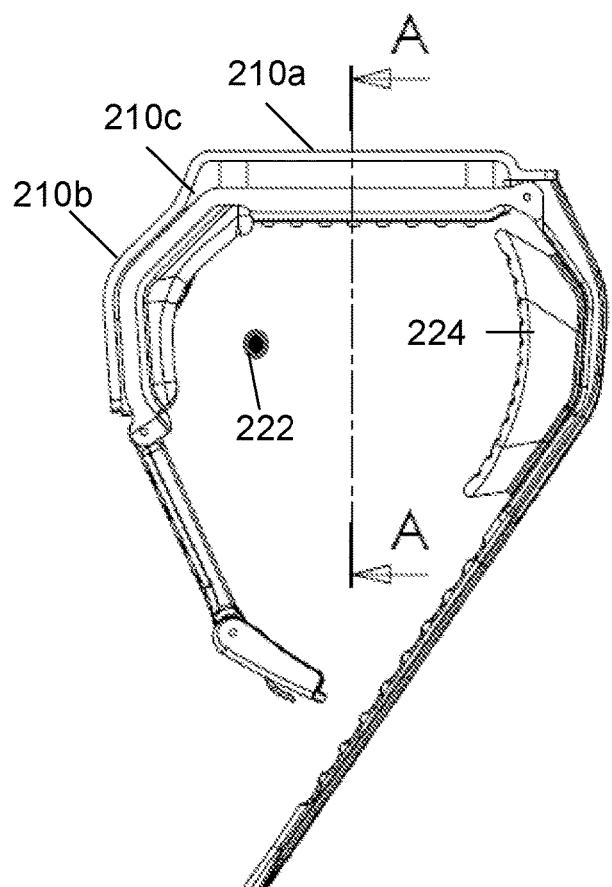
FIGS. 4A and 4B are side and perspective views, respectively, of the pulse oximeter of FIG. 2 in accordance with some embodiments of the present invention.
Figure 4B:
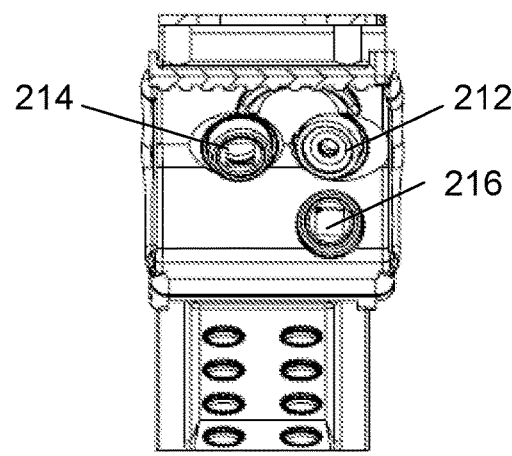

FIGS. 4A and 4B are side and perspective views, respectively, of the device of FIG. 2 in accordance with some embodiments of the present invention. In FIG. 4A, the portions 210a, 210b, and 210c of the casing of device 200 are illustrated from the side. In addition, the virtual center point of the distal end of a wearer's ulna bone is illustrated schematically as point 222. Viewing device 200 in the direction indicated by section A-A in FIG. 4A produces the view illustrated in FIG. 4B. In FIG. 4B, the light source(s) 212 and sensor(s) 214 and/or 216 are shown generally from the point of view of a wearer's wrist. As can be seen, each of 212, 214, and 216 has a different axis resulting from the manner in which each of them is angled generally toward the virtual center point 222 of the distal end of a wearer's ulna bone.

Figure 5:
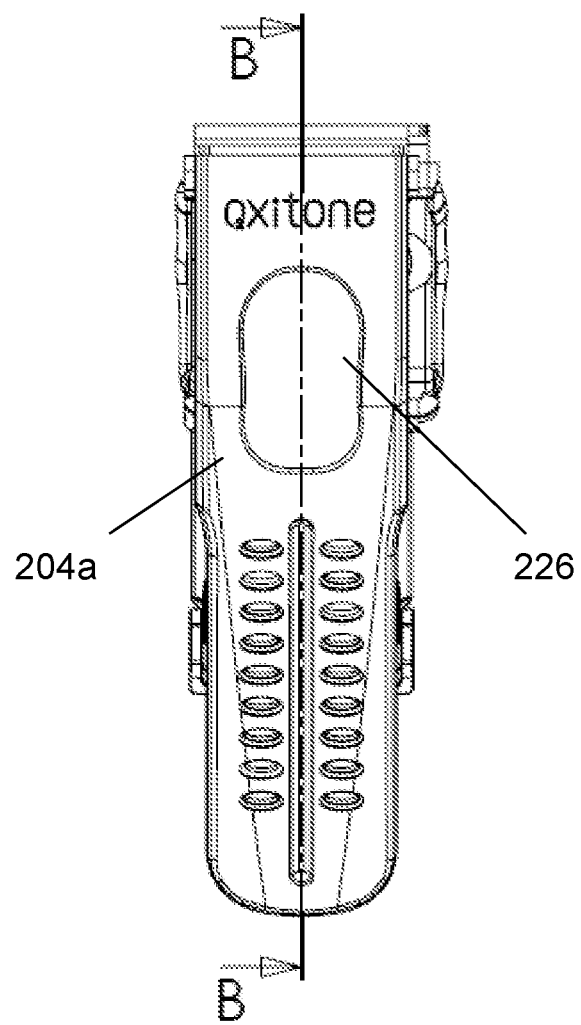
FIG. 5 is another side view of the pulse oximeter of FIG. 2 in accordance with some embodiments of the present invention.

FIG. 5 is another side view of the device of FIG. 2 in accordance with some embodiments of the present invention. FIG. 5 shows, for example, wrist strap 204a of device 200 and opening 226 through which emergency medicine (e.g., one or more pills) may be inserted to and accessed from an at least partially hollow portion of projection 208. Viewing device 200 in the direction indicated by section B-B in FIG. 5 produces the view illustrated in FIG. 4A.

Figure 6A:
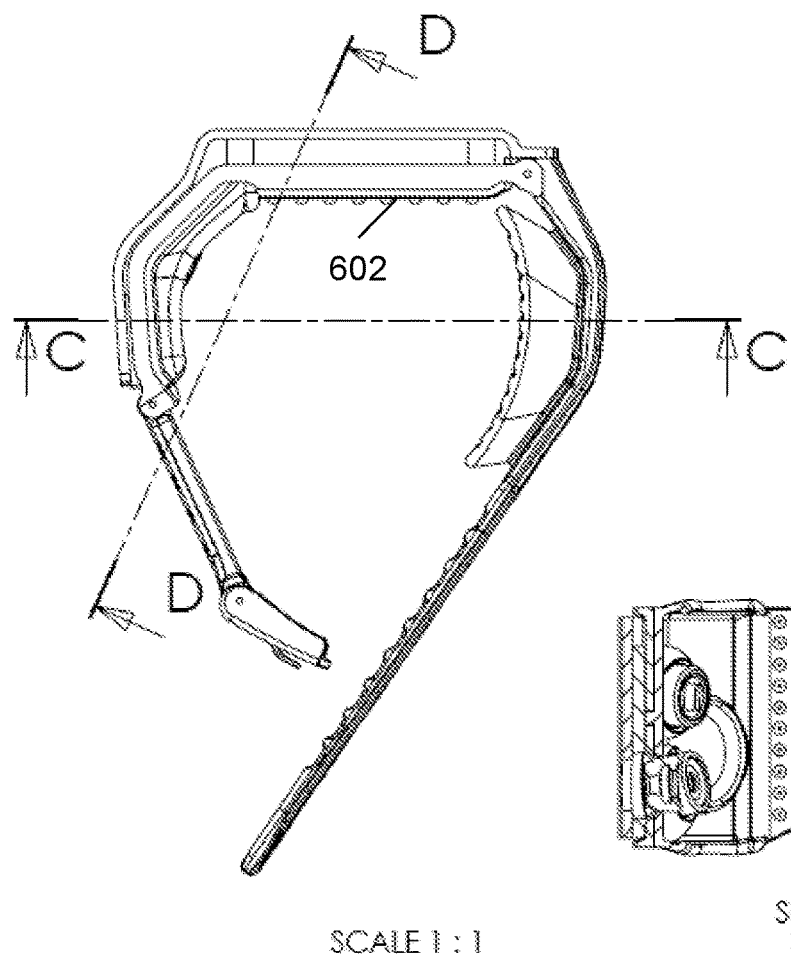
FIGS. 6A, 6B, and 6C are a side view, and two perspective views, respectively, of the pulse oximeter of FIG. 2 in accordance with some embodiments of the present invention.
Figure 6B:
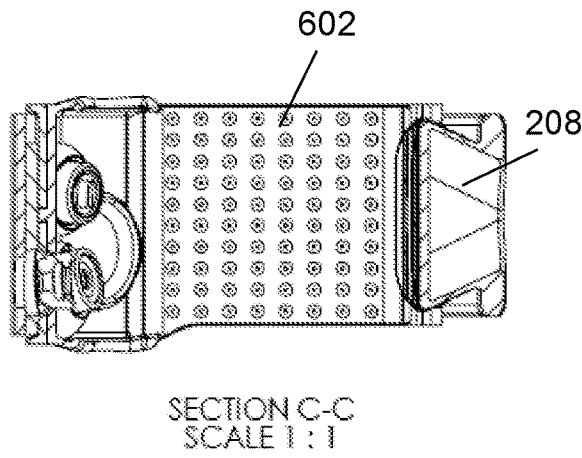
Figure 6C:
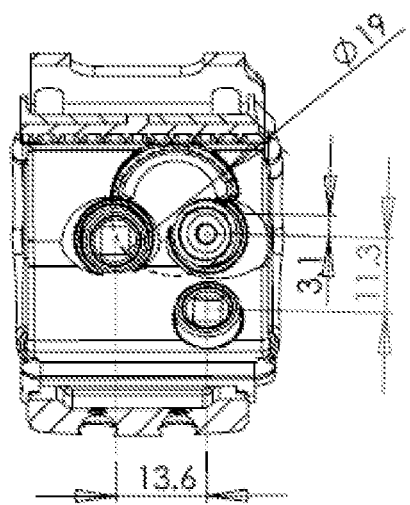

FIGS. 6A, 6B, and 6C are an additional side view, and two perspective views, respectively, of the device of FIG. 2 in accordance with some embodiments of the present invention. Viewing device 200 in the direction indicated by section C-C in FIG. 6A produces the view illustrated in FIG. 6B. In some embodiments, device 200 may include one or more projections 602 (e.g., rounded projections) that function, for example, to increase the wearer's comfort and fit of the device to the wearer's wrist. Projections 602 may be formed entirely from or otherwise include a flexible and/or stretchable material, such as rubber, silicon, soft plastic, or cloth or any combination thereof for providing the user a comfortable fit and feeling while wearing the device 200. For example, in some embodiments, projections 602 may be formed entirely from or otherwise include an elastomer material (e.g., silicon) having a softness (durometer) of between 30 to 75 Shore A (e.g., approximately 50 Shore A), which may be the same material that is used for projection 208 and/or pad 220. In other embodiments, projections 602 may be formed entirely from or otherwise include aluminum and/or thermoplastic urethane (TPU) having a durometer of, for example, between 25 Shore A and 35 Shore A (e.g., approximately 30 Shore A), which may be the same material as the casing (210a, 210b, 210c). In some embodiments, projections 602 may be formed integrally with the casing (210a, 210b, 210c).

FIG. 6C illustrates additional details regarding light source(s) 212 and sensor(s) 214 and/or 216 according to some embodiments of the present invention. Viewing device 200 in the direction indicated by section D-D in FIG. 6A produces the view illustrated in FIG. 6C. In some embodiments, the center points between light source(s) 212 and detector 216 may be approximately 11.3 millimeters (mm) apart. In other embodiments, they may be between about 7 to 15 mm apart, or about 8 to 13 mm apart. A distance between a center point of light source(s) 212 and an outer ring of light source(s) 212 may be between 1 and 8 mm, or between 1 and 4 mm (e.g., approximately 3.1 mm apart). In some embodiments, the center points between light source(s) 212 and detector 214 may be approximately 13.6 millimeters (mm) apart. In other embodiments, they may be between about 9 to 17 mm apart, or about 10 to 14 mm apart. In some embodiments, projection 218 may have a virtual circumference equal to about 19 mm, which may be generally sufficient to encompass at least parts of light source(s) 12 and/or detector 214. In other embodiments, a virtual circumference of projection 218 may be about 15 to 24 mm and may depend (e.g., be selected based on), for example, on the size of the distal end of the ulna bone of the wearer.

Figure 7:
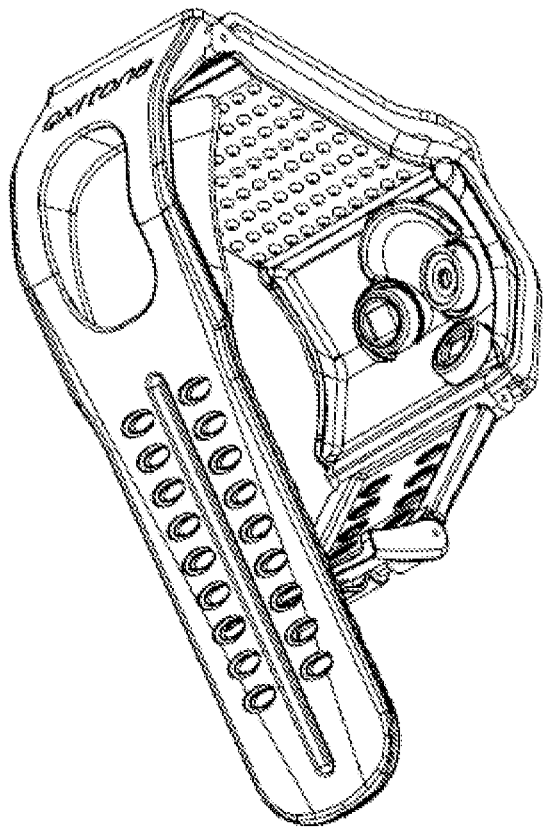
FIGS. 7 and 8 are additional perspective views of the pulse oximeter of FIG. 2 in accordance with some embodiments of the present invention.
Figure 8:
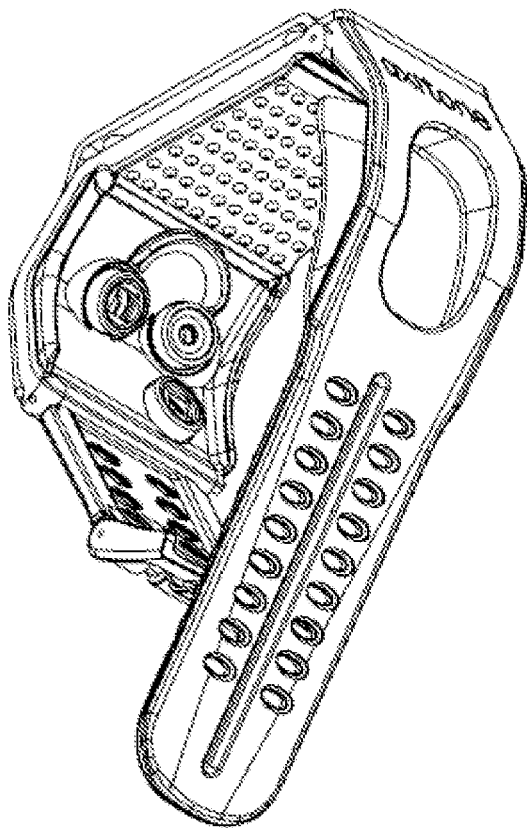

FIGS. 7 and 8 are additional perspective views of the device of FIG. 2 in accordance with some embodiments of the present invention.

Figure 9:
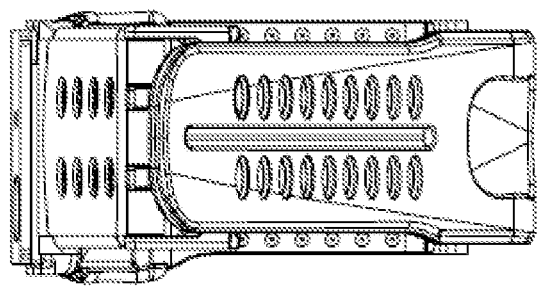
FIG. 9 is a bottom view of the pulse oximeter of FIG. 2 in accordance with some embodiments of the present invention.

FIG. 9 is a bottom view of the pulse oximeter of FIG. 2 in accordance with some embodiments of the present invention.

Figure 10:
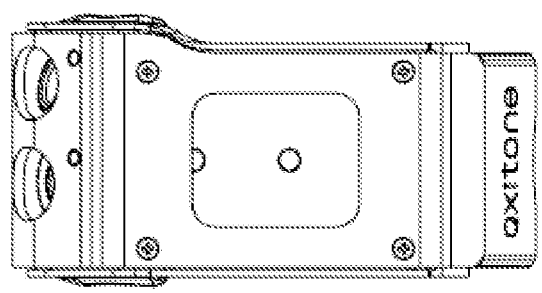
FIG. 10 is a top view of the pulse oximeter of FIG. 2 in accordance with some embodiments of the present invention.

FIG. 10 is a top view of the pulse oximeter of FIG. 2 in accordance with some embodiments of the present invention.

Figure 11:
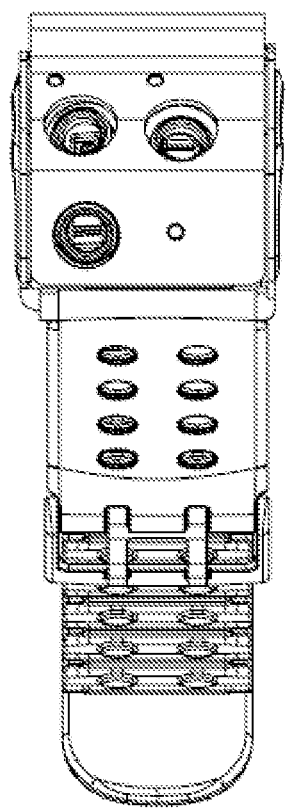
FIG. 11 is another side view of the pulse oximeter of FIG. 2 in accordance with some embodiments of the present invention.

FIG. 11 is another side view of the pulse oximeter of FIG. 2 in accordance with some embodiments of the present invention. In FIG. 11, the outermost part of the device casing is in phantom view to further illustrate the positioning of light source(s) 212, detector 214, and detector 216.

Figure 12:
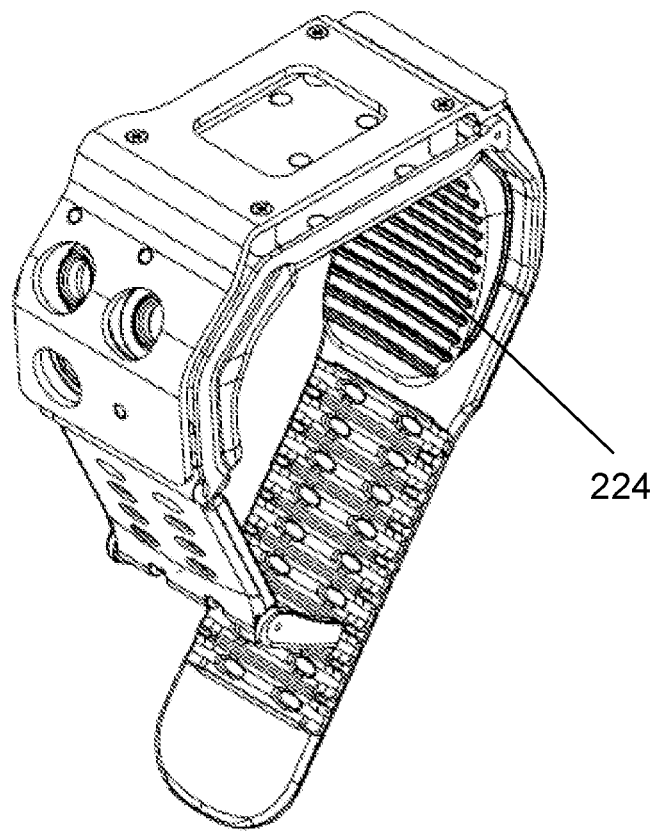
FIGS. 12 and 13 are additional perspective views of the pulse oximeter of FIG. 2 in accordance with some embodiments of the present invention.
Figure 13:
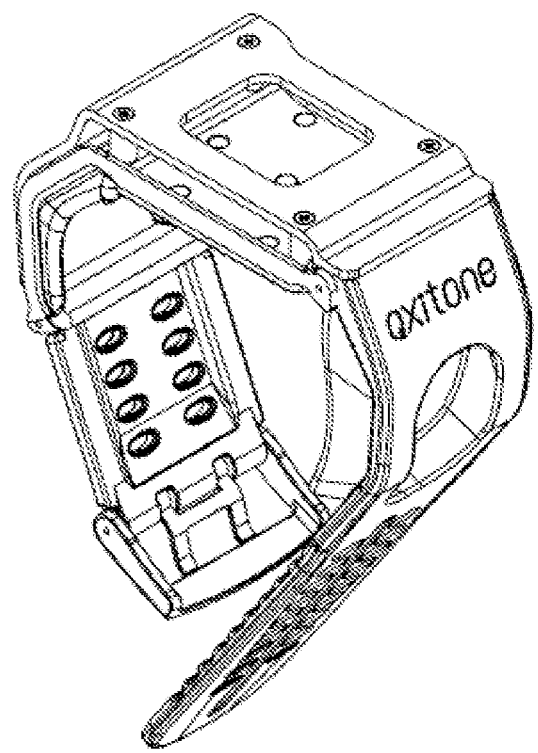

FIGS. 12 and 13 are additional perspective views of the pulse oximeter of FIG. 2 in accordance with some embodiments of the present invention. In these figures, the outermost part of the device casing and the display 202 are in phantom view to further illustrate the positioning of light source(s) 212, detector 214, and detector 216.

Figure 14:
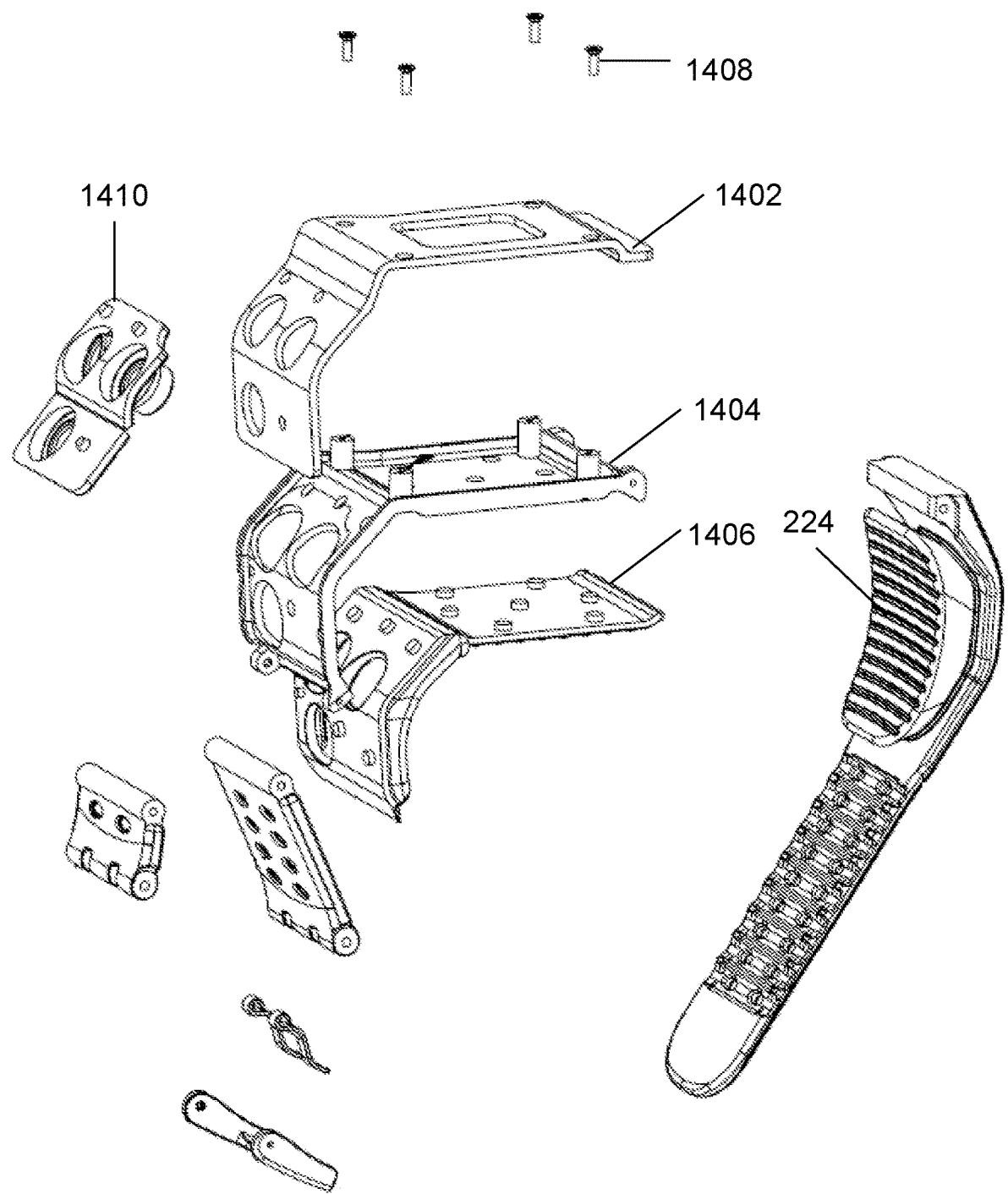
FIG. 14 is an exploded view showing various components of the pulse oximeter of FIG. 2 in accordance with some embodiments of the present invention.

FIG. 14 is an exploded view showing various components of the pulse oximeter of FIG. 2 in accordance with some embodiments of the present invention. As shown, in some embodiments, the casing (referenced above as 210a, 210b, and 210c) may include a first component 1402, second component 1404, and third component 1406. First component 1402 may be fixed to second component 1404 using one or more screws 1408 or other fixating devices. In some embodiments, third component 1406 (e.g., formed from an elastomer, for example, the same material as projection 208) may be glued or otherwise affixed to second component 1406. Component 1410 (e.g., formed from an elastomer, for example, the same material as projection 208) may include various elements for housing light source(s) 212, detector 214, and detector 216, where these elements of component 1410 that fit through corresponding openings in at least components 1404 and 1406. Component 1410 may be encased on its other side by component 1402.

Figure 15:
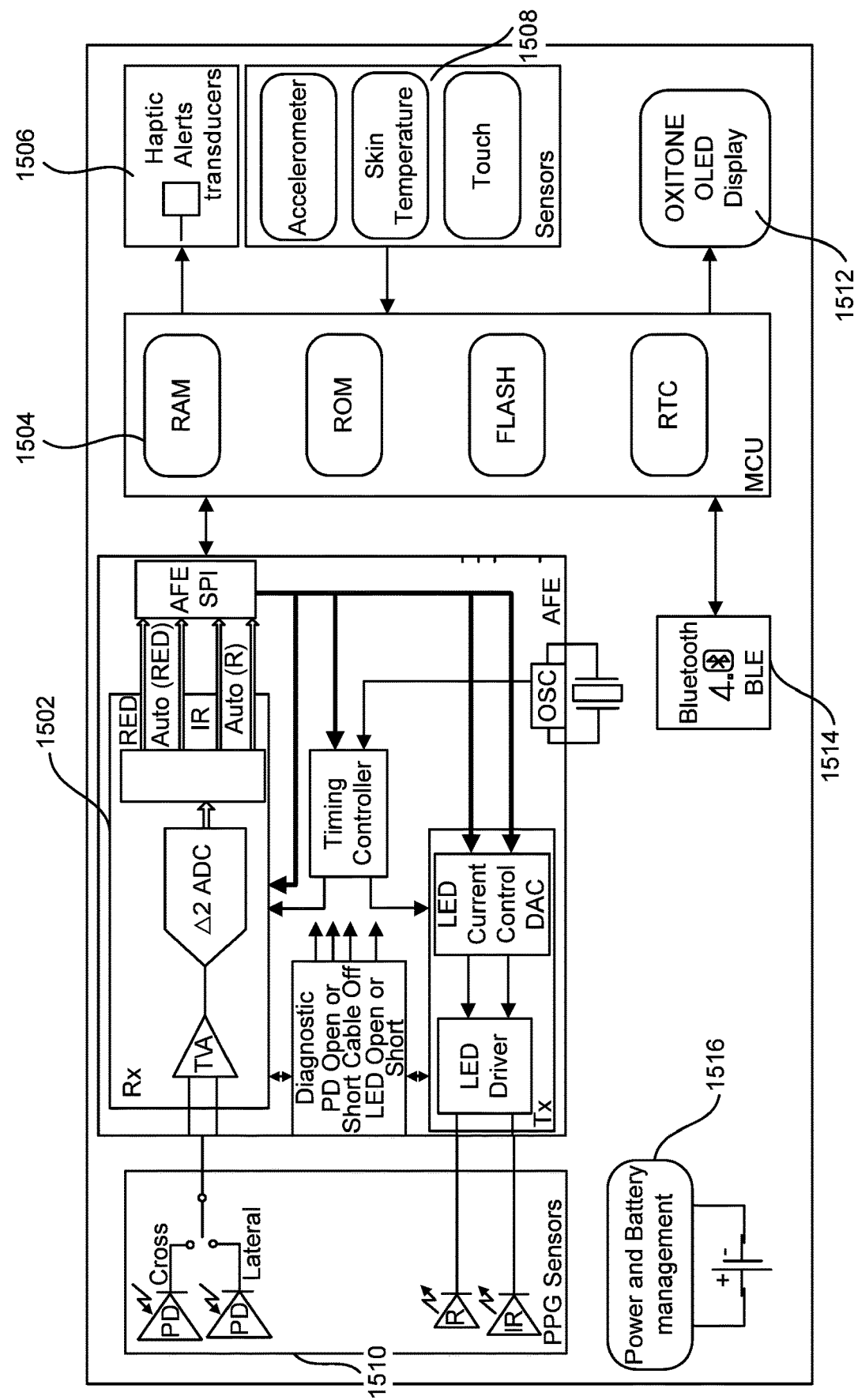
FIG. 15 is a block circuit diagram illustrating hardware functionality of the pulse oximeter of FIG. 2 in accordance with some embodiments of the present invention.

FIG. 15 is a block circuit diagram illustrating hardware functionality of the pulse oximeter of FIG. 2 in accordance with some embodiments of the present invention. In general, in some embodiments, device 200 operates to generate red and infrared optic signals, which are used for heart rate and SPO2 measurements. To enable these and other features of device 200, in some embodiments device 200 is capable of detection and measuring of incoming optic signals, movements detection, temperature sensing, signal processing, wireless transmission and receipt of data, visual display of at least heart rate, SPO2 and battery charge status, haptic alerts, battery operation, and power and battery management. FIG. 15 includes the following nine building blocks: analog front end (AFE) 1502, microcontroller unit (MCU) 1504, alerts transducers (haptic) 1506, sensors (e.g., accelerometer, skin temperature and touch) 1508, PPG sensors (e.g., LEDs and photo-diodes) 1510, display panel 1512, and wireless radio 1514 (e.g., Bluetooth), and power management circuit 1516. The device may also include a user push-button or interface control for, for example, turning the device On/Off, navigating between screens, and/or reacting to the application requests. Additional details in accordance with various embodiments of the present invention are provided below.

In some embodiments, AFE block 1502 may be a fully-integrated analog front-end (AFE) suited for pulse oximeter applications. It may include a low-noise receiver channel with an integrated analog-to-digital converter (ADC), an LED transmit section, and diagnostics for sensor and LED fault detection. AFE block 1502 may be a configurable timing controller. This flexibility may enable the user to control the device timing characteristics. To ease clocking requirements and provide a low-jitter clock, an oscillator may also be integrated that functions from an external crystal. The AFE block 1502 may communicate to an external microcontroller or host processor using a suitable interface, such as, for example, an SPI™ interface.

The MCU block 1504 according to some embodiments of the present invention, with its attached memories, may be in charge of all the control and housekeeping tasks of device 200 as well as the SPO2 and heart rate signal processing and calculations. The MCU block 1504 may store and be configured to run one or more computer programs and/or applications. The computer instructions for such programs and/or applications may be stored in one or more non-transitory computer readable media of MCU block 1504.

The alerts transducers 1506 according to some embodiments of the present invention may contain one or more haptic transducers that provide haptic alerts whenever a fault is encountered or the wearer's SPO2 level goes below a certain level.

Sensors 1508 according to some embodiments of the present invention may include some or all of the following sensors: (i) accelerometer and gyroscope to provides movements and position data; (ii) skin temperature sensor to provide skin temperature data; and (iii) a touch sensor to detect if the device is attached to a wearer's wrist or not.

Display 1512 according to some embodiments of the present invention may be an OLED display (e.g., 96×96 pixels), and may display the calculated SPO2 and heart-rate as well as one or more status symbols and error messages.

Wireless radio 1514 according to some embodiments of the present invention may implement one or more suitable wireless communication functionalit(ies) (e.g., Bluetooth 4 (BLE) standard) and may be used to establish one or more communication channels between device 200 and, for example, a dedicated control and monitoring application (e.g., running on the wearer's mobile device such as a mobile phone) and/or a remote monitoring facility accessed via the internet or a cellular communications network.

Power and battery management block 1516 according to some embodiments of the present invention may accept a suitable battery (e.g., lithium-ion polymer battery), produce all necessary voltages, charge the battery, and monitor the battery condition.

Figure 16:
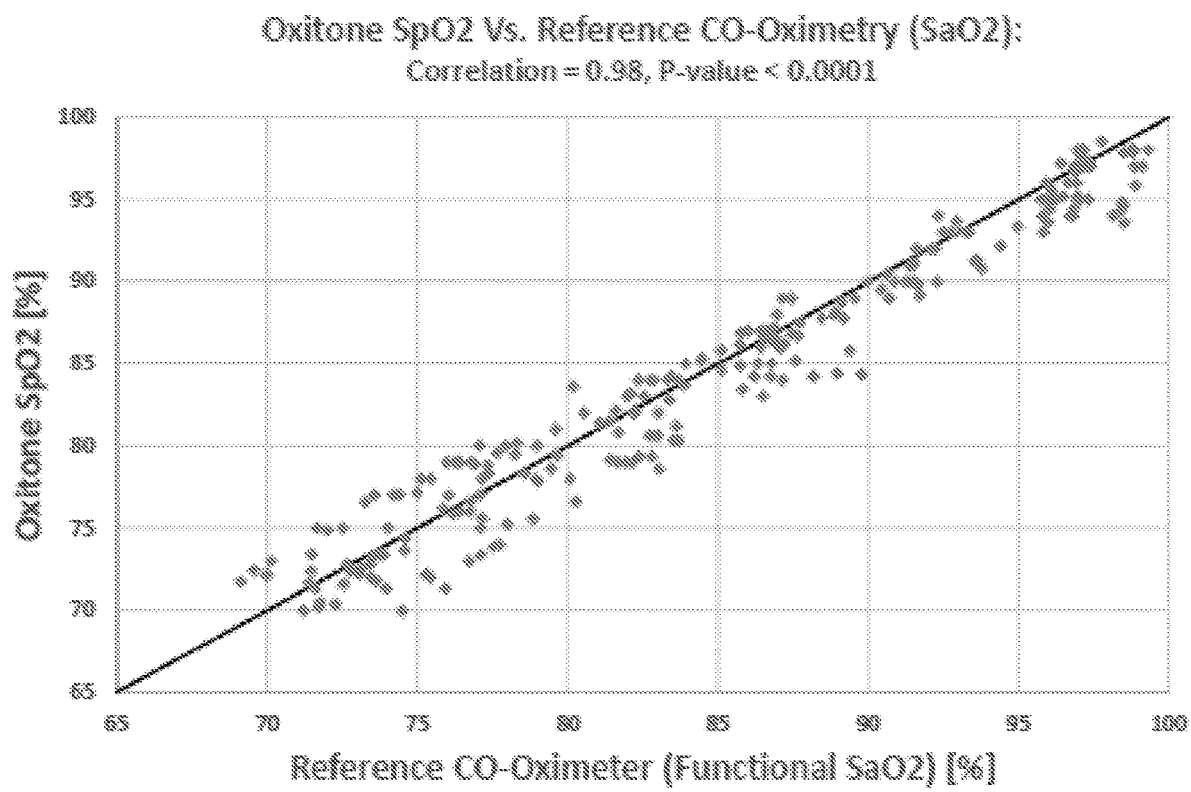
FIG. 16 is a graph demonstrating the accuracy of pulse oximetry data produced by a pulse oximeter in accordance with FIG. 2 according to some embodiments of the present invention.

FIG. 16 is a graph demonstrating the accuracy of pulse oximetry data produced by a pulse oximeter in accordance with FIG. 2 according to some embodiments of the present invention. As shown in FIG. 16, there is a tight correlation (correlation=0.98; p-value<0.0001) between the pulse oximetry data (SPO2) derived from a device generally in accordance with FIG. 2 in some embodiments of the present invention and a reference functional arterial oxygen saturation (SaO2) determined by the average of 4 independent CO-oximeters measurements.

Figure 17:
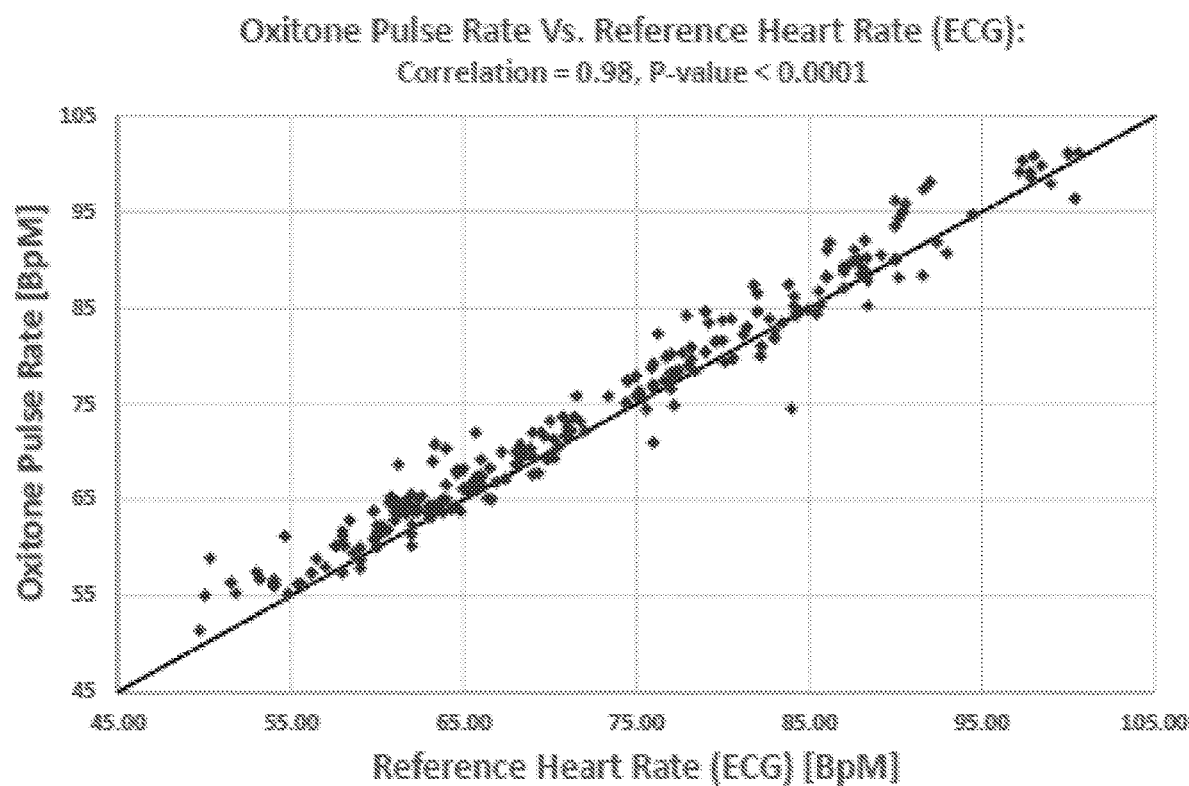
FIG. 17 is a graph demonstrating the accuracy of pulse rate data produced by a pulse oximeter in accordance with FIG. 2 according to some embodiments of the present invention.

FIG. 17 is a graph demonstrating the accuracy of pulse rate data produced by a pulse oximeter in accordance with FIG. 2 according to some embodiments of the present invention. As shown in FIG. 17, there is a tight correlation (correlation=0.98; p-value<0.0001) between the pulse rate (PR) derived from a device generally in accordance with FIG. 2 in some embodiments of the present invention and a reference heart rate (HR) determined by a standard electrocardiograph (ECG) device.

Figure 18:
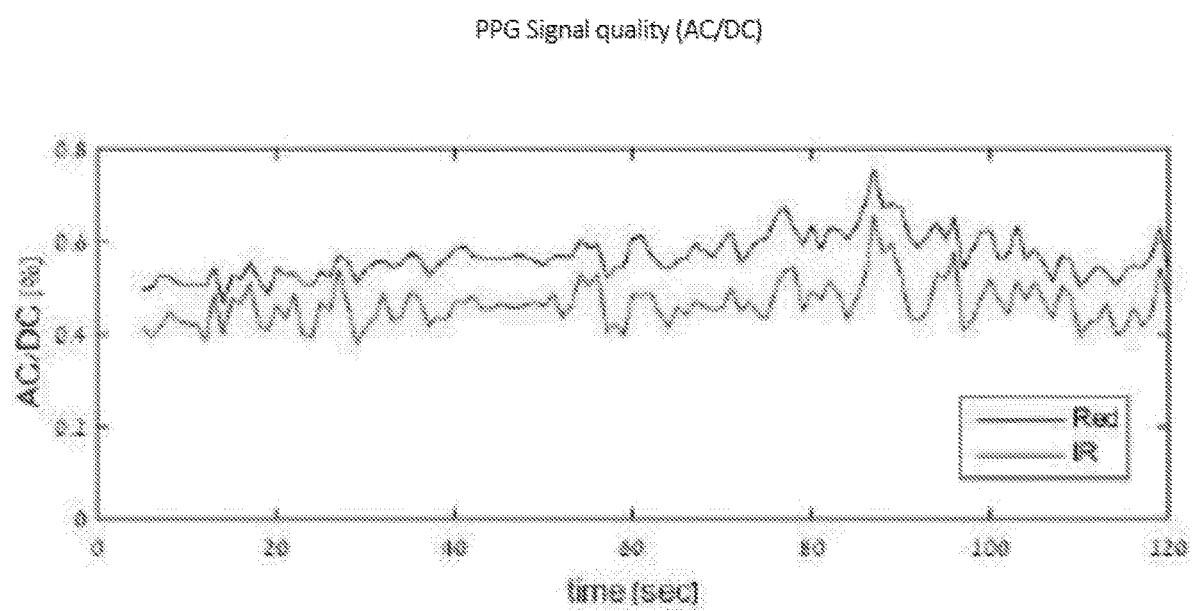
FIG. 18 is a graph of PPG signal quality by a pulse oximeter in accordance with FIG. 2 according to some embodiments of the present invention.

FIG. 18 is a graph of PPG signal quality by a pulse oximeter, for each of red and infrared light sources, in accordance with a device according to FIG. 2 in some embodiments of the present invention. The y-axis reflects the ratio of the alternating current (AC) to direct current (DC) portion of the signal, and the x-axis is time in seconds.

Figure 19A:
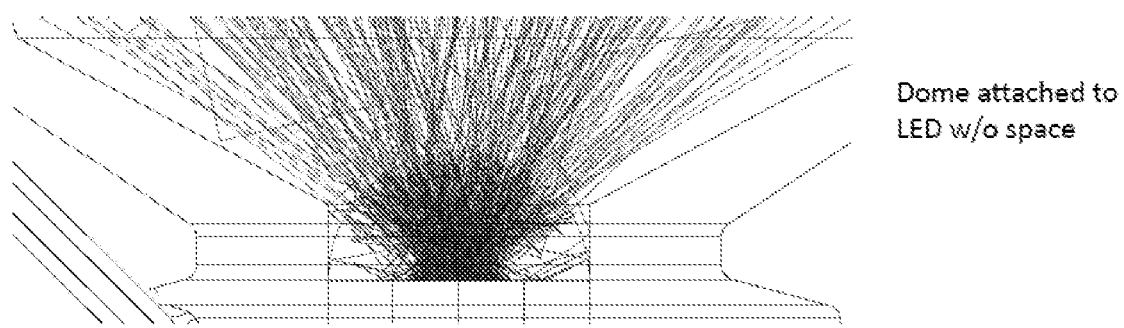
Figure 19B:
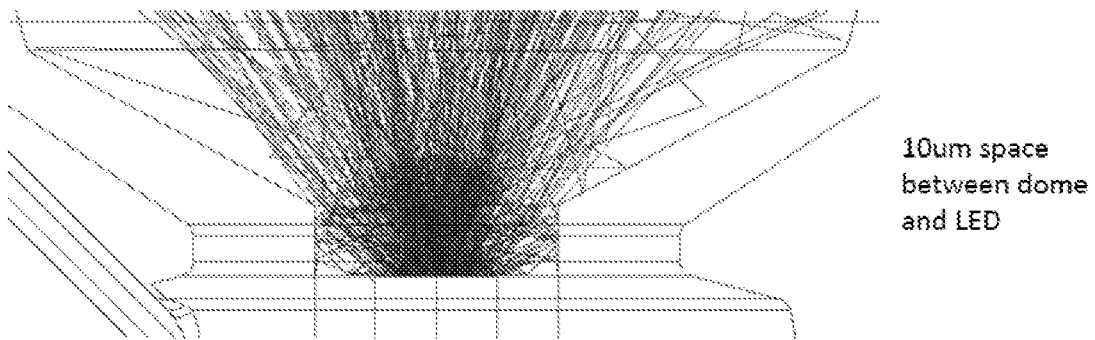

FIGS. 19A, 19B, 20A, 20B, 21A, and 21B illustrate embodiments of light source configurations for a wrist-worn pulse oximeter (e.g., configurations for light source(s) 212 of device 200 in FIG. 2) according to some embodiments of the present invention. FIGS. 19A and 19B illustrate the light that passes through a dome-shaped lens (e.g., 4 or 5 mm dome-shaped lens) that is attached to a light emitting diode (LED) without space (FIG. 19A) or with a 10 micrometer space between them (FIG. 19B). As shown, the light rays are more concentrated when there is a space between the lens and the LED. Stray light is more prevalent when there is no space between the lens and LED.

FIGS. 20A and 20B illustrate configurations for a housing for light source(s) according to some embodiments of the present invention. As shown, in both FIGS. 20A and 20B the housing includes a raised inner ring 2002 and an outer ring 2004. In some embodiments, the light source(s) (e.g., one or more LEDs) housed by the structure shown in FIGS. 20A and 20B may be placed generally within the area encompassed by inner ring 2002. In various embodiments, the light source(s) may be positioned below, equal to, or above the height of inner ring 2002.

In some embodiments, inner ring 2002 may have a height that is greater than zero but less than or equal to the height (h) of outer ring 2004. For example, in some embodiments, the height of the outer ring 2004 may be between about 1 millimeter (mm) (or less), to about 15 mm (e.g., approximately 4 mm). The height of the inner ring 2002 may be between about 1 millimeter (mm) (or less) to about 15 mm (e.g., approximately 2 mm). For example, locating the base of inner ring 2002 at half the height of outer ring 2004 may reduce stray light by approximately 40%.

In some embodiments, the housing contains an inner ring 2002 but no outer ring 2004. In some embodiments, inner ring 2002 may have a height of zero (i.e., no inner ring), in which case the light source(s) housed by the structure may be placed generally within the area encompassed by outer ring 2004, and may be positioned in various embodiments below, equal to, or above the height of outer ring 2004. In some embodiments, a housing is provided that does not contain inner ring 2002 nor outer ring 2004.

FIGS. 21A and 21B each illustrate a configuration for a housing for light source(s) according to some embodiments of the present invention. They may be the same as or similar to the housing(s) shown in FIGS. 20A and 20B, respectively, albeit in side view. As shown, in both the FIGS. 21A and 21B embodiments the housing is generally conically-shaped and extends at an angle. When the angle was increased from about 56.5 degrees to about 59 degrees (an increase of about 2.5 degrees), stray light from the light source decreased by about 80%. In other embodiments, the housing may be at least partially cylindrically-shaped. In some embodiments, a maximal diameter of the housing (measured at the top of the housing at the outer ring) may be in a range of about 1 mm (or less) to about 30 mm, or from about 5 mm to about 20 mm (e.g., about 14 mm and making an angle of about 60 degrees). In some embodiments, the housing may cover adjacent detector(s) as well (e.g., but leaving an opening over the detector(s) as partially shown in FIGS. 21A and 21B). In some embodiments, a diameter of the inner ring may be about 1 mm (or less) to about 25 mm, or from about 5 mm to about 20 mm (e.g., about 8 mm).

Figure 22:
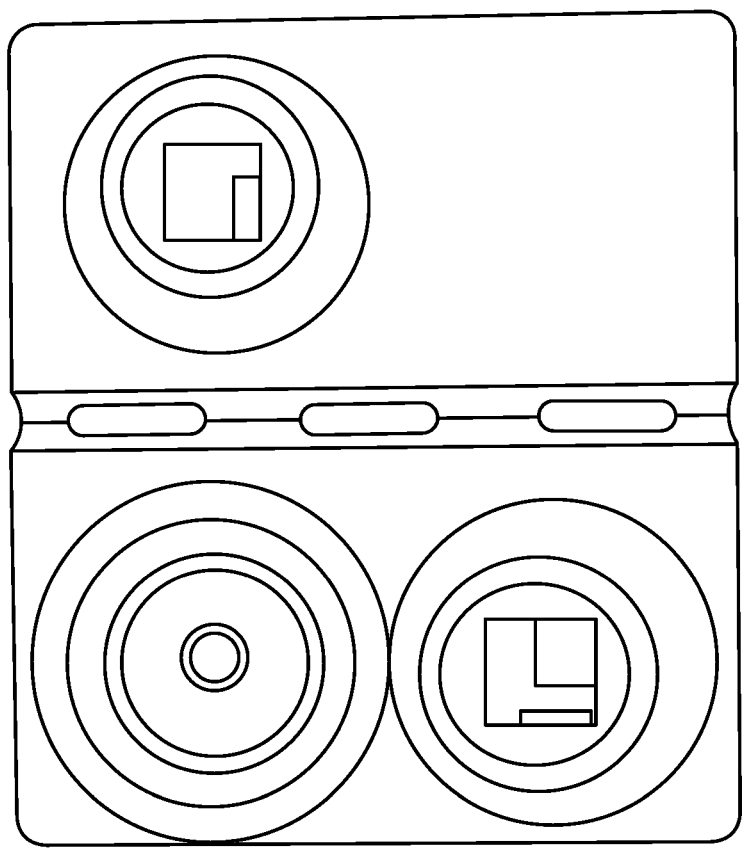
FIGS. 22 and 23 illustrate housings for light source(s) and detector(s) according to some embodiments of the present invention.
Figure 23:
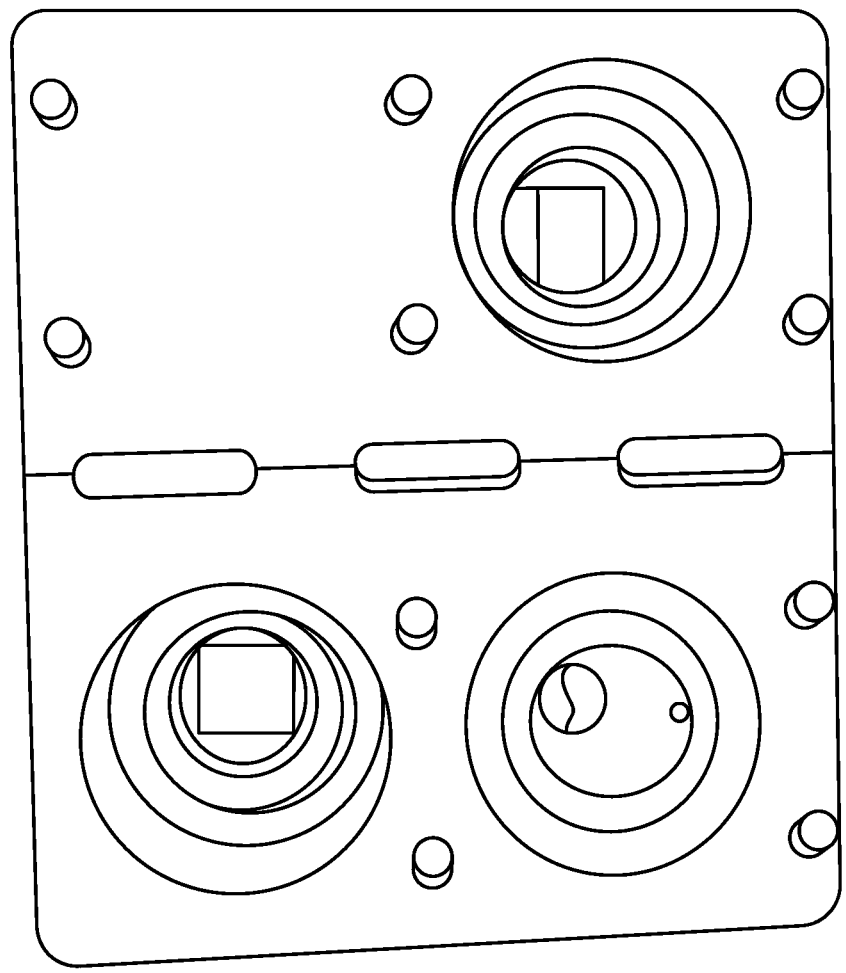

FIGS. 22 and 23 illustrate housings for light source(s) and detector(s) according to some embodiments of the present invention. These housings may be embodiments of component 1410 (FIG. 14), where the housings for the light source(s) and detector(s) are at least partially cylindrically-shaped. A front side of this component, which may be an insert for inclusion within a device (e.g., device 200), where light is emitted from is shown in FIG. 22. A rear side of this component is shown in FIG. 23. In some embodiments, such housings may have the general dimensions (e.g., in terms of height(s) and diameter(s)) described above in connection with FIGS. 20A, 20B, 21A, and 21B. In some embodiments, the inner and outer rings of the housings form a spring-like configuration (e.g., resulting from their collective configuration like a garmoshka and/or in other embodiments based on the inclusion of one or more springs). In some embodiments, the housings may be elastic, flexible, and spring-like for fixation to a wearer and/or to function as a damper to movement (artifacts) and to direct an optical axis of corresponding optical elements towards point 222 to maintain a transillumination and/or reflection configuration.

Figure 24:
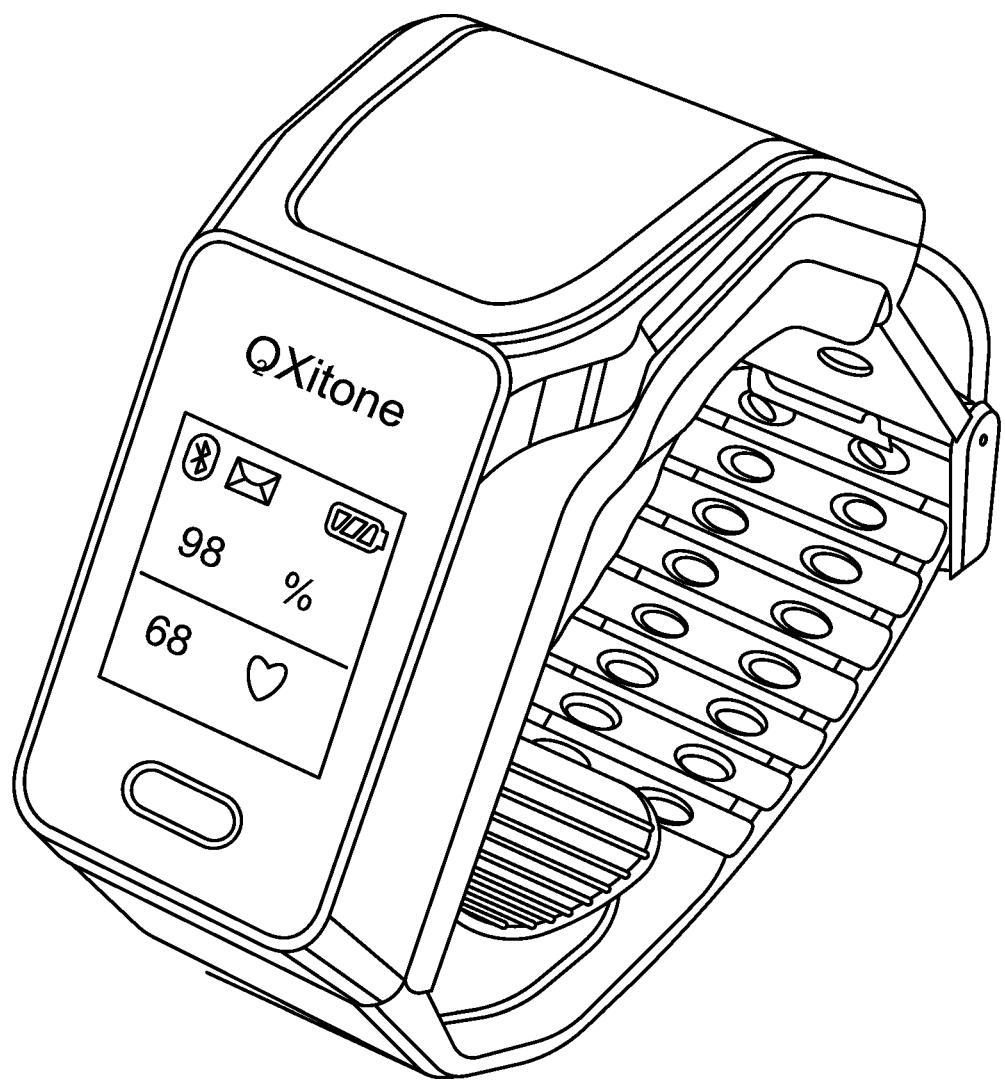
FIGS. 24 through 29 illustrate multiple views of a device (e.g., wrist-type pulse oximeter) in accordance with another embodiment of the present invention.
Figure 25:
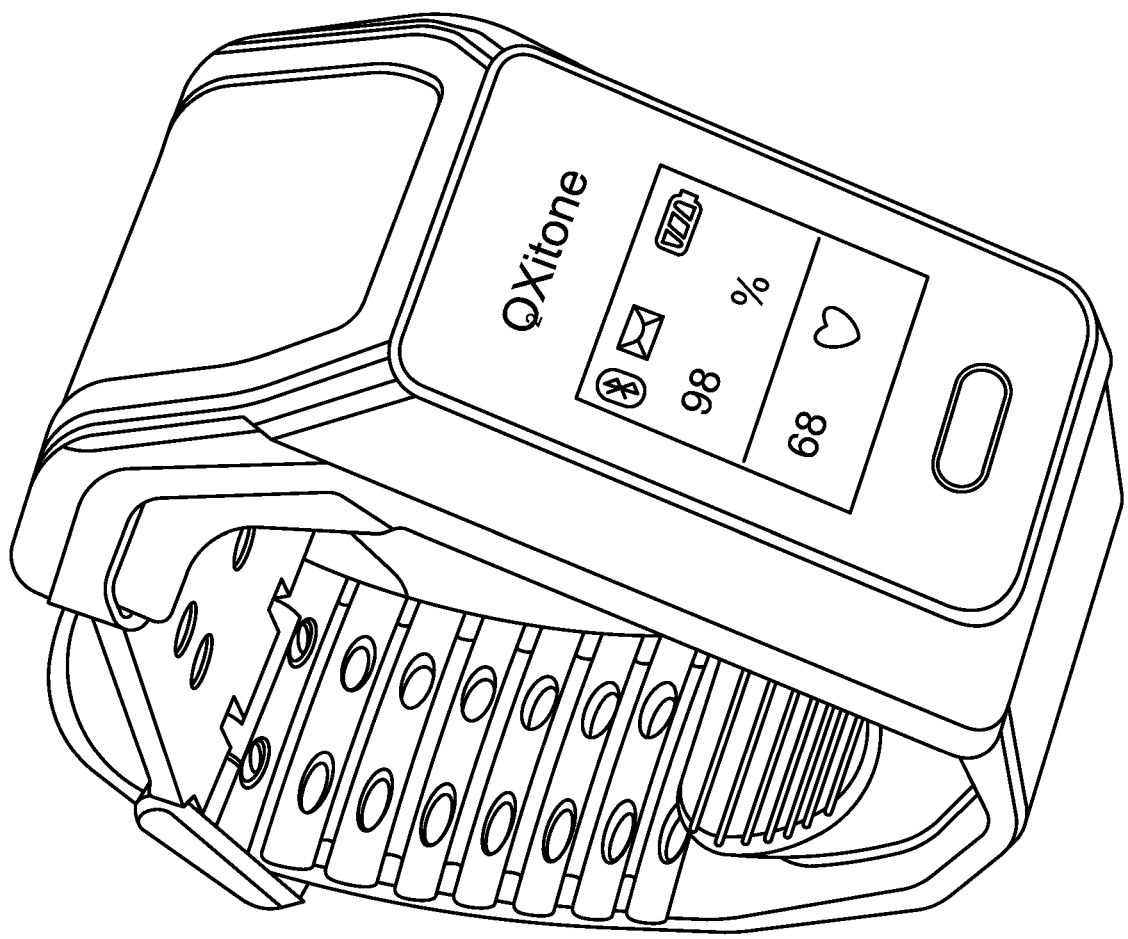
Figure 26:
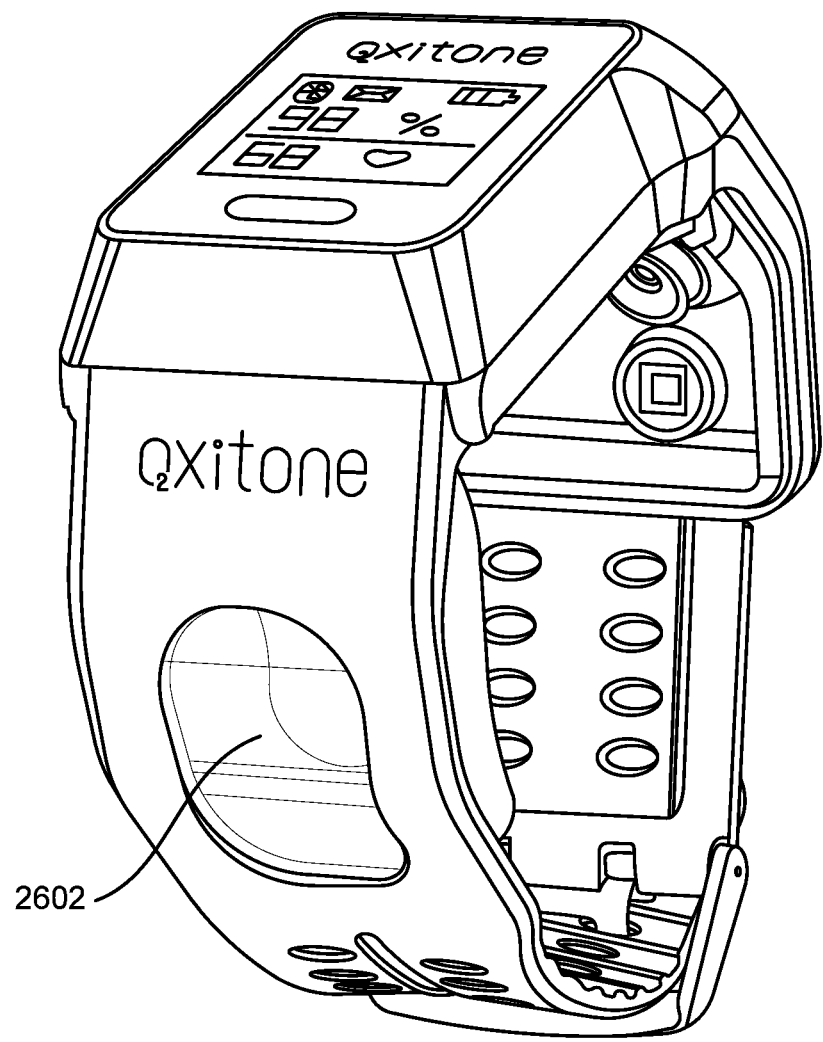
Figure 27:
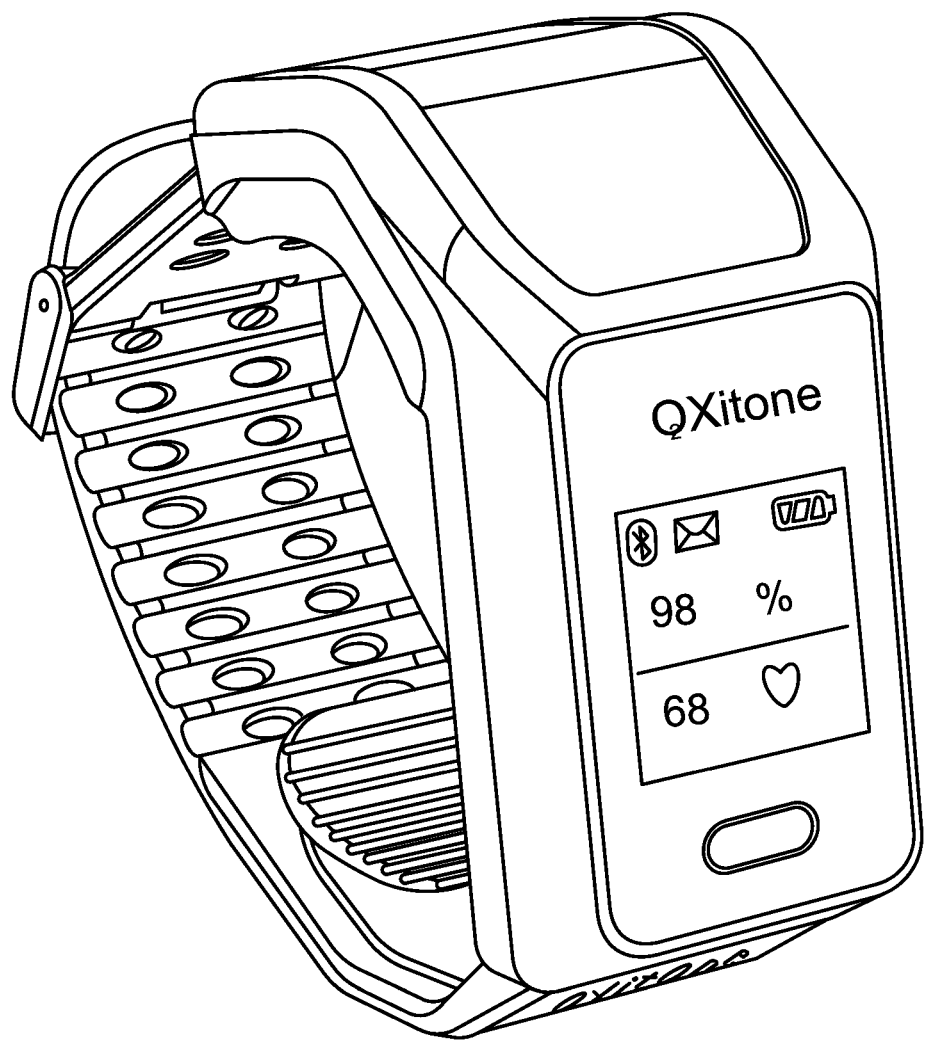
Figure 28:
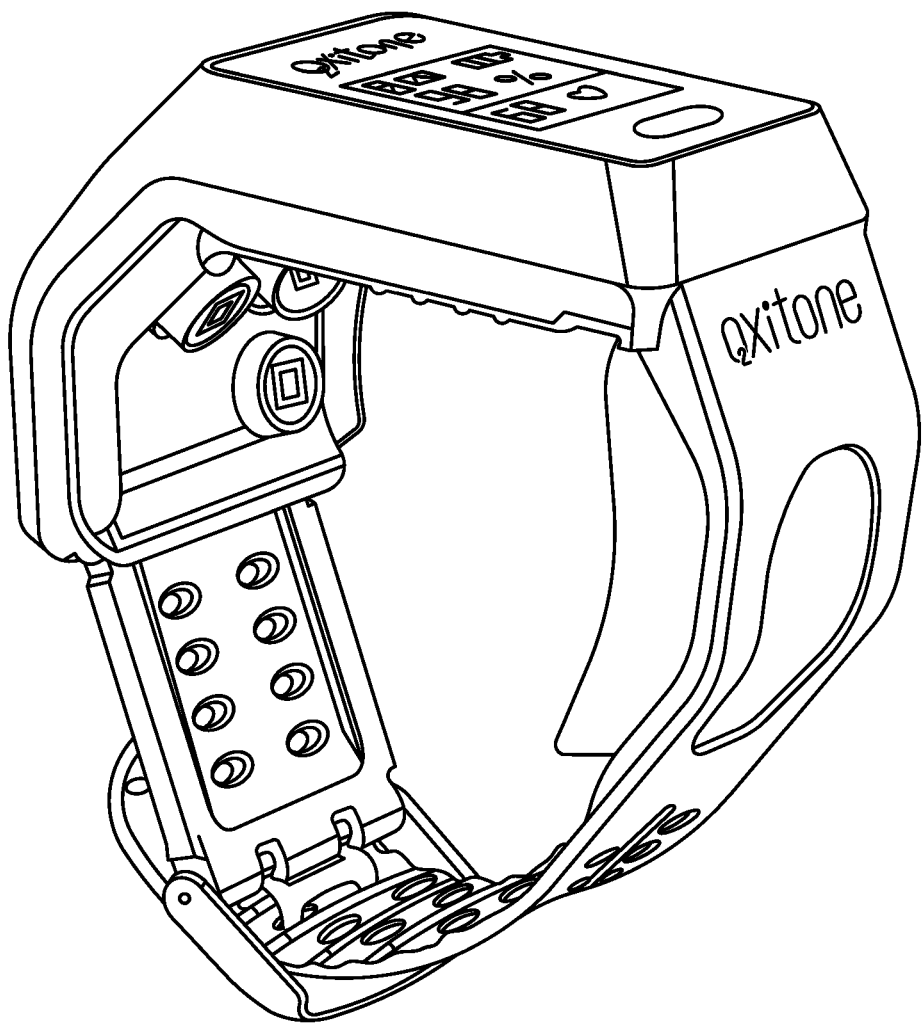
Figure 29:
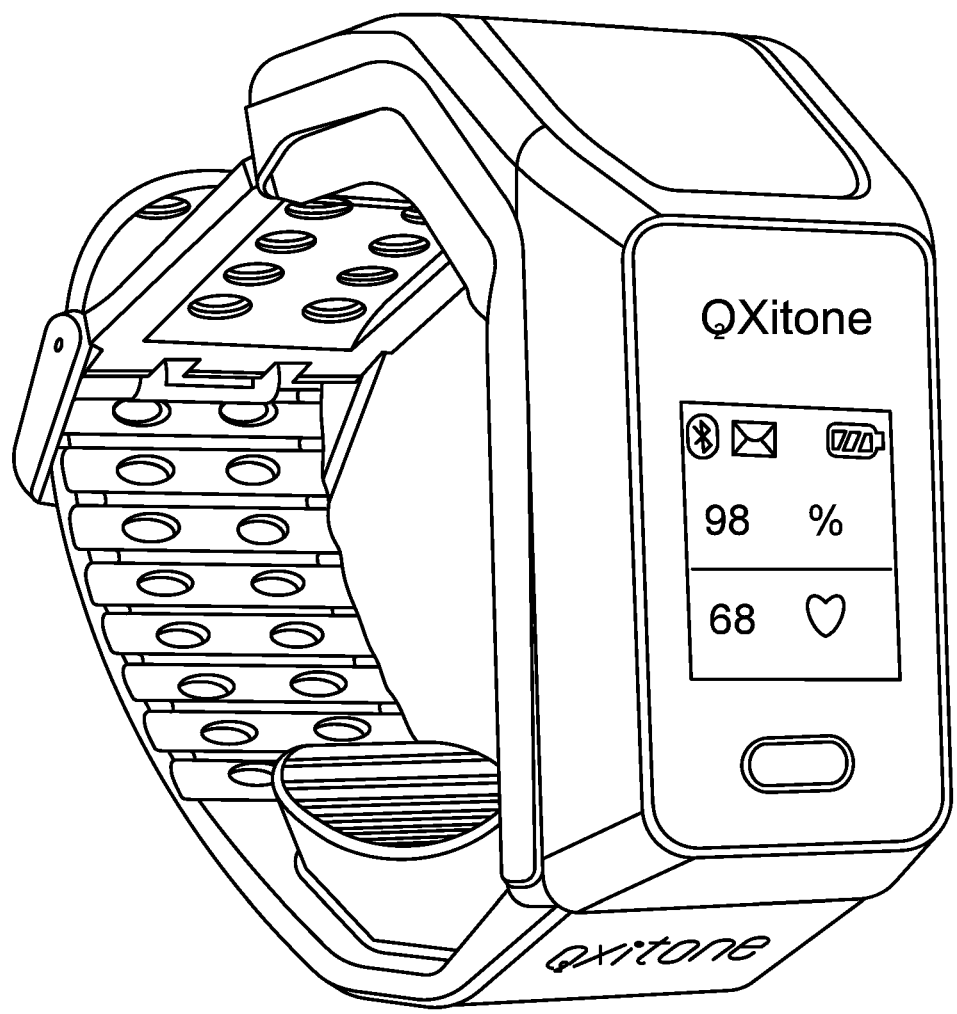

FIGS. 24 through 29 illustrate multiple views of a device (e.g., wrist-type pulse oximeter) in accordance with another embodiment of the present invention. For example, FIG. 24 illustrates that the device may measure and/or display data regarding SPO2, pulse rate, Bluetooth status, notification (envelope icon) and battery charge level. In FIG. 26, an opening 2602 (e.g., the same as or similar to opening 226) for receipt or access of emergency medication (e.g., one or more pills) may be provided. In some embodiments, the device shown in FIGS. 24 through 29 may be the same as or similar to device 200 (FIG. 2) in all other respects.

A method of oximetry measurement, according to some embodiments of the invention, includes fixating a device at an area above a distal end of the ulna. This may be carried out, for example, through the use of projection 218, projection 208, and/or one or more dome-shaped projections of light source(s) 212, detector 214, and/or detector 216. Thereafter, one or more detectors at, adjacent to, or at a periphery of the fixated area may detect reflections of light by the distal end of the ulna, wherein the light was emitted by one or more (e.g., at least two) light sources having different wave lengths at, adjacent to, or at a periphery of the fixated area. In some embodiments, the detecting and emitting may be performed by detector(s) 214 and/or 216, and one or more emitter(s) 212, each having a different axis resulting from the manner in which each of them is angled generally toward a virtual center point 222 of the distal end of a wearer's ulna bone. In some embodiments, the method may further include blocking stray light from entering the fixated area, for example, by one or more projections 220. In some embodiments, the method may further comprise measuring a pulse by reflecting a coherent light source off a bone.

In the above description, an embodiment is an example or implementation of the invention. The various appearances of "one embodiment", "an embodiment" or "some embodiments" do not necessarily all refer to the same embodiments.

Although various features of embodiments of the present invention may be described in the context of a single embodiment, the features may also be provided separately or in any suitable combination. Conversely, although embodiments of the present invention may be described herein in the context of separate embodiments for clarity, the invention may also be implemented in a single embodiment.

Embodiments of the invention may include features from different embodiments disclosed above, and embodiments may incorporate elements from other embodiments disclosed above. The disclosure of elements of some embodiments of the invention in the context of a specific embodiment is not to be taken as limiting their used in the specific embodiment alone.

Furthermore, it is to be understood that embodiments of the invention can be carried out or practiced in various ways and that embodiments of the invention can be implemented in other ways than the ones outlined in the description above.

The invention is not limited to the diagrams or to the corresponding descriptions contained herein. For example, in a method according to some embodiments of the present invention, the flow need not move through each illustrated step or state, or in exactly the same order as described.

Meanings of technical and scientific terms used herein are to be commonly understood as by one of ordinary skill in the art to which the invention belongs, unless otherwise defined.

While this specification refers to a limited number of embodiments, these should not be construed as limitations on the scope of the invention, but rather as exemplifications of some of the preferred embodiments. Other possible variations, modifications, and applications are also within the scope of embodiments of the present invention.

What is claimed is:

1. . A pulse oximetry device, the device comprising:
   at least two light sources having different wavelengths;
   at least one detector responsive to said different wavelengths;
   a wrist strap; and
   a casing coupled to the wrist strap for housing the at least two light sources and the at least one detector;
   wherein the wrist strap comprises a generally concave projection adapted to fit snugly against a wearer's wrist and remain in place even when the wearer is moving,
   wherein the generally concave projection further comprises a portion facing the wearer's wrist, and
   wherein the portion facing the wearer's wrist further comprises one or more ridges.

2. The pulse oximetry device of claim 1, wherein the generally concave projection comprises an elastomer material having a softness (durometer) of between 30 to 75 Shore A.

3. The pulse oximetry device of claim 1, wherein the generally concave projection comprises a silicon elastomer material having a softness (durometer) of approximately 50 Shore A.

4. The pulse oximetry device of claim 1, wherein the generally concave projection comprises a hollow interior portion for receipt of medication.

5. The pulse oximetry device of claim 1, wherein the wrist strap comprises:
   a first portion that comprises the generally concave projection; and
   a second portion adapted for attachment to the first portion for fixating the wrist strap around a user's wrist, and wherein the second portion comprises a second projection that assists to fixate the device at a fixated area corresponding to a distal end of the wearer's ulna bone.

6. The pulse oximetry device of claim 5, wherein the second projection is a curved projection that generally follows a contour of the wearer's ulna bone.

7. The pulse oximetry device of claim 6, wherein the second projection is formed generally in the shape of part of a dome or sphere.

8. The pulse oximetry device of claim 1, wherein each of the at least two light sources and the at least one detector is positioned within the casing such that when the wrist strap is affixed around the wearer's wrist the at least two light sources and the at least one detector are positioned adjacent to the distal end of the ulna and closer to the ulna than the radius, and the at least one detector is positioned to detect light emitted from the at least two light sources.

9. The pulse oximetry device of claim 1, further comprising a pad that is mounted or otherwise fixed generally to an inner side of the casing, wherein said pad comprises one or more barriers that function to fit snugly against a wearer's wrist and prevent stray light from entering a measuring area of the at least two light sources and the at least one detector when the pulse oximetry device is worn by a wearer.

10. A pulse oximetry device, the device comprising:
    at least two light sources having different wavelengths;
    at least one detector responsive to said different wavelengths;
    a wrist strap; and
    a casing coupled to the wrist strap for housing the at least two light sources and the at least one detector, wherein the wrist strap includes a generally concave projection adapted to fit snugly against a wearer's wrist, the generally concave projection includes a portion facing the wearer's wrist having one or more ridges;
    wherein each of the at least two light sources and the at least one detector is angled generally toward a virtual center point of the distal end of a wearer's ulna bone and each of the at least two light sources and the at least one detector has a different axis, and
    wherein the virtual center point is located a spaced distance apart from a surface of the wearer's ulna bone.

11. The pulse oximetry device of claim 10, wherein each of the at least two light sources and the at least one detector is positioned within the casing such that when the wrist strap is affixed around the wearer's wrist the at least two light sources and the at least one detector are positioned adjacent to the distal end of the ulna and closer to the ulna than the radius, and the at least one detector is positioned to detect light emitted from the at least two light sources.

12. The pulse oximetry device of claim 10, wherein at least one of the at least two light sources and the at least one detector comprises a generally dome-shaped or conical-shaped structure that assists to fixate the pulse oximetry device, and its corresponding at least two light source(s) and at least one detector, at a fixated area corresponding to a distal end of a wearer's ulna bone.

13. A pulse oximetry device, the device comprising:
    at least two light sources having different wavelengths;
    at least one detector responsive to said different wavelengths;
    a wrist strap; and
    a casing coupled to the wrist strap for housing the at least two light sources and the at least one detector;
    wherein the casing comprises a first portion and a second portion that extend at an angle relative to each other, with a display fixed to the first portion and the at least two light sources and the at least one detector fixed to the second portion, and
    wherein the first portion and the second portion of the casing are integrally formed;
    wherein the first portion of the casing and the second portion of the casing together are generally "L" shaped.

14. The pulse oximetry device of claim 13, wherein the casing is strong enough to maintain the positioning of the at least two light sources and the at least one detector when the device is worn by a wearer, while simultaneously having pliability or elasticity to act as a movement dampening cushion that reduces measurement artifacts of the pulse oximetry device resulting from movement of the wearer.

15. The pulse oximetry device of claim 14, wherein the casing comprises a third portion that joins the first portion and the second portion of the casing, where the third portion allows for angular movement between the first portion and the second portion of the casing in response to normal forces while the pulse oximetry device is being worn by a user.

16. The pulse oximetry device of claim 13, wherein the casing comprises aluminum or thermoplastic urethane (TPU).

17. The pulse oximetry device of claim 16, wherein the casing has a durometer of between 25 Shore A and 35 Shore A.

18. The pulse oximetry device of claim 13, wherein each of the at least two light sources and the at least one detector is positioned within the casing such that when the wrist strap is affixed around the wearer's wrist the at least two light sources and the at least one detector are positioned adjacent to the distal end of the ulna and closer to the ulna than the radius, and the at least one detector is positioned to detect light emitted from the at least two light sources.

* * * * *